(12) United States Patent
Reed

(10) Patent No.: US 11,835,500 B2
(45) Date of Patent: Dec. 5, 2023

(54) DEVICE AND METHOD FOR CHANGING SOLUTION CONDITIONS IN SERIAL FLOW

(71) Applicant: ADMINISTRATORS OF THE TULANE EDUCATIONAL FUND, New Orleans, LA (US)

(72) Inventor: Wayne F. Reed, New Orleans, LA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 623 days.

(21) Appl. No.: 15/518,658

(22) PCT Filed: Oct. 13, 2015

(86) PCT No.: PCT/US2015/055204
§ 371 (c)(1),
(2) Date: Apr. 12, 2017

(87) PCT Pub. No.: WO2016/061024
PCT Pub. Date: Apr. 21, 2016

(65) Prior Publication Data
US 2017/0234842 A1   Aug. 17, 2017

Related U.S. Application Data

(60) Provisional application No. 62/063,020, filed on Oct. 13, 2014.

(51) Int. Cl.
*C08F 2/00* (2006.01)
*B01J 19/24* (2006.01)
(Continued)

(52) U.S. Cl.
CPC ............ *G01N 30/78* (2013.01); *B01F 33/811* (2022.01); *B01F 35/2132* (2022.01);
(Continued)

(58) Field of Classification Search
None
See application file for complete search history.

(56) References Cited

U.S. PATENT DOCUMENTS 3,230,047 A   1/1966   Weinbrenner
4,153,766 A * 5/1979   Koide .................. B01J 19/0006
                                                  526/59
(Continued)

FOREIGN PATENT DOCUMENTS

EP   2169010 A2   3/2010
JP   2002-517527 A   6/2002
(Continued)

OTHER PUBLICATIONS

Alb et al., Simultaneous continuous, nonchromatographic monitoring and discrete chromatographic monitoring of polymerization reactions, J. Appl. Polymer Sci., 13:190-8 (2009).
(Continued)

*Primary Examiner* — Neil N Turk
(74) *Attorney, Agent, or Firm* — MARSHALL, GERSTEIN & BORUN LLP

(57) ABSTRACT

Disclosed herein is a device and method for changing the conditions of a solution flowing in a serial path. In particular, disclosed herein is a device that includes a chemical reactor, a first system, and a second system that are each serial to one another. Each of the first system and the second system include a mixing chamber, a solvent reservoir, a solvent pump, and one or more detectors. Also disclosed herein is a method for changing the condition of a solution that includes flowing a liquid sample in a path, serially mixing the sample with at least two discrete solvents while it flows through the path, and detecting the condition of the sample after it is mixed with each solvent.

14 Claims, 6 Drawing Sheets

(51) Int. Cl.
| | |
|---|---|
| *B01J 19/00* | (2006.01) |
| *B01F 33/81* | (2022.01) |
| *B01F 33/80* | (2022.01) |
| *G01N 30/78* | (2006.01) |
| *B01J 4/00* | (2006.01) |
| *B01F 35/21* | (2022.01) |
| *B01F 35/71* | (2022.01) |
| *C12M 1/34* | (2006.01) |
| *G01N 1/38* | (2006.01) |
| *G01N 15/02* | (2006.01) |
| *G01N 15/00* | (2006.01) |

(52) U.S. Cl.
CPC ...... *B01F 35/2133* (2022.01); *B01F 35/7176* (2022.01); *B01J 4/00* (2013.01); *B01J 19/0093* (2013.01); *B01J 19/245* (2013.01); *C12M 1/34* (2013.01); *B01D 2313/08* (2013.01); *B01F 33/834* (2022.01); *B01J 2219/00813* (2013.01); *B01J 2219/00867* (2013.01); *B01J 2219/00871* (2013.01); *B01J 2219/00889* (2013.01); *B01J 2219/00894* (2013.01); *B01J 2219/00952* (2013.01); *B01J 2219/00968* (2013.01); *B01J 2219/00997* (2013.01); *G01N 1/38* (2013.01); *G01N 15/02* (2013.01); *G01N 2015/0092* (2013.01)

(56) References Cited

U.S. PATENT DOCUMENTS

| | | | | |
|---|---|---|---|---|
| 4,572,819 | A * | 2/1986 | Priddy | B01J 19/0006 422/111 |
| 5,756,883 | A * | 5/1998 | Forbes | G01N 11/06 73/54.04 |
| 6,052,184 | A | 4/2000 | Reed | |
| 6,610,816 | B2 * | 8/2003 | Kurose | C08G 69/04 528/310 |
| 6,618,144 | B1 | 9/2003 | Reed | |
| 6,653,150 | B1 | 11/2003 | Reed | |
| 7,716,969 | B2 | 5/2010 | Reed et al. | |
| 8,322,199 | B2 | 12/2012 | Reed | |
| 2001/0037674 | A1 * | 11/2001 | Petro | B01D 15/08 73/61.52 |
| 2002/0082383 | A1 | 6/2002 | Kurose et al. | |
| 2004/0004717 | A1 | 1/2004 | Reed | |
| 2004/0013587 | A1 | 1/2004 | Holl et al. | |
| 2004/0115838 | A1 | 6/2004 | Quake et al. | |
| 2004/0136902 | A1 | 7/2004 | Plath et al. | |
| 2005/0090630 | A1 | 4/2005 | Mackenzie et al. | |
| 2005/0211242 | A9 | 9/2005 | Plath | |
| 2006/0210438 | A1 | 9/2006 | Nagai et al. | |
| 2008/0216563 | A1 | 9/2008 | Reed et al. | |
| 2009/0240011 | A1 | 9/2009 | Hillairet et al. | |
| 2009/0306311 | A1 | 12/2009 | Reed | |
| 2014/0080115 | A1 | 3/2014 | Reed | |
| 2014/0296472 | A1 | 10/2014 | Kaushiva | |

FOREIGN PATENT DOCUMENTS

| | | |
|---|---|---|
| JP | 2002-194079 A | 7/2002 |
| JP | 2007-009151 A | 1/2007 |
| WO | WO-02/053810 A1 | 7/2002 |
| WO | WO-2004/092908 A2 | 10/2004 |
| WO | WO-2009/149328 A2 | 12/2009 |
| WO | WO-2012/112545 A2 | 8/2012 |
| WO | WO-2015/026984 A1 | 2/2015 |

OTHER PUBLICATIONS

Barner et al., Complex macromolecular architectures by reversible addition fragmentation chain transfer chemistry: theory and practice, Macromol. Rapid Commun., 28:539-59 (2007).
Braunecker et al., Controlled/living radical polymerization: Features, developments, and perspectives, 32:93-146 (2007).
Catalgil-Giz et al., Online Monitoring of Composition, Sequence Length, and Molecular Weight Distributions during Free Radical Copolymerization, and Subsequent Determination of Reactivity Ratios, Macromolecules, 35(17):6557-71 (2002).
Chen et al., Synthesis and characterization of a pentaerythritol-based amphiphilic star block copolymer and its application in controlled drug release, Reactive and Functional Polymers, 69(2):97-104 (2009).
Chung et al., Thermo-responsive drug delivery from polymeric micelles constructed using block copolymers of poly(N-isopropylacrylamide) and poly(butylmethacrylate), J. Control. Release, 62(1-2):115-27 (1999).
De Las Heras Alarcon et al., Stimuli responsive polymers for biomedical applications, Chem. Soc. Rev., 34(3):276-85 (2005).
Foerster et al., Polyelectrolytes in solution, Adv. Polym. Sci., 120:53-95 (1995).
Hawker et al., New polymer synthesis by nitroxide mediated living radical polymerizations, Chem. Rev., 101(12):3661-88 (2001).
Heredia et al., Aminooxy End-Functionalized Polymers Synthesized by ATRP for Chemoselective Conjugation to Proteins, Macromolecules, 40(14):4772-9 (2007).
International Search Report and Written Opinion, International Application No. PCT/US2015/055204, dated Jan. 7, 2016.
Jain et al., On the origins of morphological complexity in block copolymer surfactants, Science, 300(5618):460-4 (2003).
Jaycox, Stimuli-responsive polymers. 9. Photo-regulation of optical rotations in chiral polyesters: Altering responsive outputs with conformationally flexible backbone elements, Polymer, 48:82-90 (2007).
Jeong et al., Lessons from nature: stimuli-responsive polymers and their biomedical applications, Trends Biotechnol., 20(7):305-11 (2002).
Kulkarni et al., Micro and nanoscale smart polymer technologies in biomedicine, pp. 289-304, in: Desai et al. (eds.), BioMEMS and Biomedical Nanotechnology, vol. III: Therapeutic Micro/Nanotechnology (2007).
Lele et al., Synthesis of Uniform Protein-Polymer Conjugates, Biomacromolecules, 6(6):3380-7 (2005).
Li et al., Moderation of the Interactions between Sodium Dodecyl Sulfate and Poly(vinylpyrrolidone) Using the Nonionic Surfactant Hexaethyleneglycol Mono-n-dodecyl Ether $C_{12}EO_6$: an Electromotive Force, Microcalorimetry, and Small-Angle Neutron Scattering Study, Langmuir, 16(23):8677-84 (2000).
Liu et al., Recent advances and challenges in designing stimuli-responsive polymers, Prog. Polymer Sci., 35:3-23 (2010).
Lochhead, The role of polymers in cosmetics: recent trends, pp. 3-56 in: Morgan et al. (eds.), Cosmetic Nanotechnology: Polymers and Colloids in Cosmetics, ACS Symposium Series (2007).
Matyjaszewski et al., Comparison and classification of controlled/living radical polymerizations, pp. 2-26 in: Matyjaszewski (ed.), Controlled/Living Radical Polymerization, Progress in ATRP, NMP, and RAFT, ACS Symposium Series, vol. 768, (2000).
Matyjaszewski et al., Gradient copolymers by atom transfer radical copolymerization, J. Phys. Org. Chem., 13:775-86 (2000).
Mayadunne et al., Mechanistic and practical aspects of RAFT polymerization, p. 65, in: Jagur-Grodzinski (ed.), *Living and Controlled Polymerization: Synthesis, Characterization and Properties of the Respective Polymers and Copolymers*, New York: Nova Science Publishers (2005).
Maynard et al., Thermoresponsive biohybrid materials synthesized by ATRP, J. Mater. Chem., 17:4015-7 (2007).
McFaul et al., Online, continuous monitoring of the sensitivity of the LCST of NIPAM-Am copolymers to discrete and broad composition distributions, Polymer 55(19):4899-907 (2014).
McFaul et al., Simultaneous multiple sample light scattering detection of LCST during copolymer synthesis, Polymer, 52(21):4825-33 (2011).
Moad et al., Living radical polymerization by the RAFT process—a first update, Aust. J. Chem., 59:669-92 (2006).
Nath et al., Creating "Smart" Surfaces Using Stimuli Responsive Polymers, Adv. Mater., 14:1243-7 (2002).

(56) References Cited

OTHER PUBLICATIONS

Norwood et al., Comparison of On-line Single-Capillary and Bridge Capillary Viscometric Detectors for Size Exclusion Chromatography, Int. J. Polymer Anal. Characterization, 4(2):99-132 (1997).

Paril et al., Online Monitoring of the Evolution of Polyelectrolyte Characteristics during Postpolymerization Modification Processes, Macromolecules, 40(13):4409-13 (2007).

Park et al., Sustained Release Control via Photo-Cross-Linking of Polyelectrolyte Layer-by-Layer Hollow Capsules, Langmuir, 21(12):5272-7 (2005).

Purcell et al., Adsorption of Sodium Dodecyl Sulfate at the Surface of Aqueous Solutions of Poly(vinylpyrrolidone) Studied by Neutron Reflection, Langmuir, 14(7):1637-45 (1998).

Raez et al., A reversible tube-to-rod transition in a block copolymer micelle, J. Am. Chem. Soc., 125(32):9546-7 (2003).

Richter et al., Mechanically adjustable chemostats based on stimuli-responsive polymers, Sensors and Actuators B Chemical, 21:5272-7 (2007).

Schmaljohann, Thermo- and pH-responsive polymers in drug delivery, Adv. Drug Deliv. Rev., 58(15):1655-70 (2006).

Sorci et al., Electrostatic and Association Phenomena in Aggregates of Polymers and Micelles, Langmuir, 18(2):353-64 (2002).

Strelitzki et al., Automated batch characterization of polymer solutions by static light scattering and viscometry, J. Appl. Polymer Sci., 73(12):2359-67 (1999).

Tang et al., Solubilization and Controlled Release of a Hydrophobic Drug Using Novel Micelle-Forming ABC Triblock Copolymers, Biomacromolecules, 4(6):1636-45 (2003).

Teoh et al., Atom Transfer Radical Copolymerization of Hydroxyethyl Methacrylate and Dimethylaminoethyl Methacrylate in Polar Solvents, Macromolecules, 39(25):8609-15 (2006).

Winnick et al., Stimuli-Responsive Materials: Polymers, Colloids, and Multicomponent Systems, Langmuir, 23(1):1-2 (2007).

Zhang et al., Synthesis and Characterization of pH- and Temperature-Sensitive Poly(methacrylic acid)/Poly(N-isopropylacrylamide) Interpenetrating Polymeric Networks, Macromolecules, 33(1):102-7 (2000).

Zhuang et al., Multi-stimuli responsive macromolecules and their assemblies, Chem. Soc. Rev., 432:7421-35 (2013).

Australian Patent Application No. 2015333761, Examination Report No. 1, dated Apr. 14, 2021.

European Patent Application No. 15850092.6, Extended European Search Report, dated Mar. 14, 2018.

\* cited by examiner

DEVICE AND METHOD FOR CHANGING SOLUTION CONDITIONS IN SERIAL FLOW

CROSS-REFERENCE TO RELATED APPLICATION

The benefit under 35 U.S.C. § 119(e) of U.S. Provisional Patent Application Ser. No. 62/063,020 filed Oct. 13, 2014, is hereby claimed, and the disclosure thereof is hereby incorporated herein by reference.

STATEMENT OF GOVERNMENT SUPPORT

This invention was made in-part with government support under EPS-1430280, awarded by the U.S. National Science Foundation. The Government has certain rights in the invention.

BACKGROUND

Technical Field

The present disclosure relates to the formulation of solution conditions in a serial path allowing increments of formulation additives, such as but not limited to electrolytes, acids, bases, surfactants, small molecules, fluorescent dyes, drugs, chelating agents, polymers, colloids to be added in serial fashion with a detector stage at each formulation step monitoring the effect of each additive. In particular, the present disclosure relates to a device and method for changing the conditions of a solution flowing in a serial path, and for detecting properties of the solution as it flows through the path.

Description of Related Technology

The ability to monitor a chemical reaction as it is occurring, such as determining the characteristics and interactions of a polymer during polymer, polymerization, and postpolymerization reactions, reduces costs and increases reaction efficiencies. Polymer 'reactions' include those in which polymers and/or colloids are produced, modified, or interact chemically or physically with themselves or other species. Polymerization reactions include but are not limited to polycondensation, free and controlled radical polymerization (CRP), and non-covalent polymerization reactions. See References 1-8. Postpolymerization modifications include functionalization of polymers with charged groups, grafts, and biomolecules, such as through bioconjugation. See References 1-3. Polymer interactions include surfactant association with neutral polymers to form charged structures (see References 1-4, and self-assembled structures that trap and release substances. See References 1-3.

Devices have been developed that allow the continuous monitoring of polymerization reactions. See e.g., U.S. Pat. Nos. 653,150 and 8,322,199, each of which is incorporated herein by reference in its entirety. These Automatic Continuous Online Monitoring of Polymerization Reactions ("ACOMP") systems avoid intermediate process steps by substituting 'fluid-fluid' sample handling. In the 'First Generation ACOMP' ("FGA"), reactor fluid is continuously extracted, diluted, and conditioned to produce a diluted stream. Intermediate solid phases are avoided, and high dilutions (to 1000× and higher) can change solvent by reducing the original solvent to a tiny admixture. Such extraction/dilution/conditioning can take 10 to 200 seconds.

The Second Generation ACOMP system ("SGA") is specifically designed to measure the onset and evolution of polymer stimuli responsiveness during the synthesis of stimuli responsive polymers. See WO 2009/149328; McFaul, Cohn A. et al., "Simultaneous Multiple Sample Light Scattering Detection Of LCST During Copolymer Synthesis", Polymer, 2011, 4825-4833; Reed, Wayne F. et al., "Online, continuous monitoring of the sensitivity of the LCST of NIPAM-Am copolymers to discrete and broad composition distributions", Polymer, 2014, 4899-4907. FIG. 1 shows a FGA system described in U.S. Pat. Nos. 6,653, 150; 8,322,199; and 6,052,184, each of which is incorporated by reference in its entirety, which feeds into a SGA. The diagram shows a serial mode of operation (with lines emanating from the series delivery pump), where the solvent condition remains the same throughout the N-detector train stages, but stimuli such as temperature, irradiation by light, ultrasound, etc. can vary from stage to stage. The diagram also shows a parallel flow system that is used in order to vary the solution condition, which involves a completely separate flow path. The serial and parallel flow paths can be toggled between by means of a signal to a solenoid diverter valve ('sol' in the figure). The parallel-flow mode of operation requires that liquid withdrawn from the reactor enter the parallel delivery pump which parcels it out into N separate streams, where N is the number of detector trains. A multihead peristaltic pump is then used to mix solvents of desired different compositions individually with each of the N streams. The use of this parallel method requires N times more withdrawal from the reactor than use of the serial method. N will generally be a number such as 8 or 16, so the consumption from the reaction will be an order of magnitude greater in parallel mode than in serial mode. Furthermore, the parallel mode requires a separate delivery pump capable of driving N streams in parallel to be mixed with the N different solvents.

The parallel flow design of FIG. 1, exhibits some deficiencies with respect to complexity, cost, performance, and efficiency. There is a need for a system that allows the automatic, continuous monitoring during chemical reactions of reaction products and intermediates under a variety of solution conditions, simultaneously, such as polymerization reactions. There is a need for such monitoring of chemical reaction products and intermediates under simultaneous different solution conditions to be carried out with simplicity, lower cost, higher performance, and increased efficiency.

SUMMARY

The present disclosure provides a device and methods of use for changing solution conditions of a liquid stream in serial flow in discrete increments, interposing one or more detectors in the serial flow path between the incremental changes to the solution.

It is an object of the disclosure to provide a means of determining the properties of the solution, including but not limited to the state of polymers or colloids contained in the solution.

It is an additional object of this disclosure to provide a more concise, economical, practical, and efficient way of providing solutions of multiple conditions in a single serial flow, rather than using individual, parallel mixing stages to obtain multiple solution conditions for measurement.

In one aspect, the disclosure provides a device that includes:

(a) a sample reservoir (e.g., a chemical reactor or an injection loop) adapted to contain a sample;

(b) a first system that includes: (i) a first mixing chamber adapted to contain a first mixing chamber solution; (ii) a first sample pump adapted to deliver the sample from the sample reservoir into the first mixing chamber; (iii) a first solvent reservoir adapted to contain a first solvent; (iv) a first solvent pump adapted to deliver the first solvent from the first solvent reservoir into the first mixing chamber; and (v) a first detector in fluid communication with the first mixing chamber; and (c) a second system serial to the first system, the second system including: (i) a second mixing chamber downstream of, and in fluid communication with, the first detector, and adapted to contain a second mixing chamber solution; (ii) a second solvent reservoir adapted to contain a second solvent; (iii) a second solvent pump adapted to deliver the second solvent from the second solvent reservoir into the second mixing chamber; and (iv) a second detector in fluid communication with the second mixing chamber.

In some embodiments, the device further includes a third system serial to the second system, the third system including: (i) a third mixing chamber downstream of, and in fluid communication with, the second detector, and adapted to contain a third mixing chamber solution; (ii) a third solvent reservoir adapted to contain a third solvent; (iii) a third solvent pump adapted to deliver the third solvent from the third solvent reservoir into the third mixing chamber; and (iv) a third detector in fluid communication with the third mixing chamber.

In some cases, the device can further include one or more additional systems in a serial path, each system including a mixing chamber, a solvent reservoir, a solvent pump, and at least one detector. The number of systems included in the device depends on the particular application for which it is being used. There is no limit to the number of systems that the device can have in a serial path.

In various cases, the device further includes one or more additional detectors. In various cases, the one or more additional detector is positioned between the sample reservoir and the first mixing chamber, and is in fluid communication with the sample reservoir and the first mixing chamber. In some embodiments, the one or more additional detector is positioned downstream to, and in fluid communication with, the first mixing chamber, the second mixing chamber, or the third mixing chamber (when present). In some cases, the detectors present in a particular system are in communication with each other.

In various embodiments, each detector is a type selected from the group consisting of light scattering, ultraviolet/visible absorption, infrared absorption, refractometry, viscosity, conductivity, pH, polarimetry, turbidity, fluorescence, circular dichroism, Raman scattering, and birefringence. In some cases, each system of the device (e.g., the first system, the second system, the third system) includes at least two detectors. In some embodiments, the at least two detectors detect light scattering and viscosity. In various embodiments, the at least two detectors detect the same property under different conditions (e.g., at different temperatures).

In various cases, the device includes at least one additional sample pump that is adapted to deliver a mixing chamber solution from a mixing chamber to a detector. In various embodiments, the at least one additional sample pump is adapted to deliver the first mixing chamber solution from the first mixing chamber to the first detector, the second mixing chamber solution from the second mixing chamber to the second detector, or the third mixing chamber solution from the third mixing chamber to the third detector (when present).

In some cases, the device further includes a conditioning component positioned between the first mixing chamber and the first detector, the second mixing chamber and the second detector, or the third mixing chamber and the third detector (when present). The conditioning component can condition the first mixing chamber solution or the second mixing chamber solution to a pre-selected condition. In various cases, the device further includes a first conditioning component positioned between the first mixing chamber and the first detector that can condition the first mixing chamber solution, and a second conditioning component positioned between the second mixing chamber and the second detector that can condition the second mixing chamber solution.

In various cases the sample comprises a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, metal ion, a chelating agent, a fluorescent dye, or combinations thereof. For example, the sample can include a polymer, a monomer, or combinations thereof.

In some cases, the device is in fluid communication with a First Generation Automatic Continuous Online Monitoring of Polymerization Reactions ("FGA") system. In various cases, the FGA system is in fluid communication with a mixing chamber.

In another aspect, the disclosure provides a method that includes: (a) flowing a sample from a sample reservoir into a first mixing chamber; (b) flowing a first solvent into the first mixing chamber; (c) mixing the sample and the first solvent to form a first mixing chamber solution; (d) flowing the first mixing chamber solution through a first detector to detect a property of the first mixing chamber solution; (e) flowing the first mixing chamber solution from the first detector to a second mixing chamber; (f) flowing a second solvent into the second mixing chamber, wherein the second solvent is nonidentical to the first solvent; (g) mixing the first mixing chamber solution and the second solvent to form a second mixing chamber solution; and (h) flowing the second mixing chamber solution through a second detector to detect a property of the second mixing chamber solution.

In some embodiments, the method further includes flowing the sample from the sample reservoir to a detector prior to flowing the sample into the first mixing chamber.

In various embodiments, the method further includes: (i) flowing the second mixing chamber solution from the second detector to a third mixing chamber; (j) flowing a third solvent into the third mixing chamber; (k) mixing the second mixing chamber solution and the third solvent to form a third mixing chamber solution; and (l) flowing the third mixing chamber solution through a third detector to detect a property of the third mixing chamber solution. In some embodiments, the method further includes flowing the sample solution through more than three additional systems in a serial path (e.g., through four, five, six, seven, eight, nine, ten, or more systems). The number of systems through which the sample solution is flowed through depends on the particular application for which the method is being practiced. There is no limit to the number of mixing chambers and solution conditions through which a sample solution can be flowed in a serial path.

In some cases, the method includes flowing at least one of the first mixing chamber solution, the second mixing chamber solution, or the third mixing chamber solution (when present) through one or more additional detectors. For example, the first mixing chamber solution, the second mixing chamber solution, or the third mixing chamber solution (when present) can each flow through at least two detectors. In various cases, the at least two detectors detect the same property under different conditions.

In some embodiments, the method further includes flowing a mixing chamber solution (e.g., a first mixing chamber solution, a second mixing chamber solution, a third mixing chamber solution (when present) to a FGA.

In various embodiments, the method further includes conditioning at least one of the first mixing chamber solution, the second mixing chamber solution, or the third mixing chamber solution (when present) prior to flowing through the first detector, the second detector, or the third detector, respectively.

In various cases, the sample from the chemical reactor includes a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a fluorescent dye, a chelating agent, a metal ion, or combinations thereof. For example, the sample from the chemical reactor can include a polymer, a monomer, or a combination thereof.

In some embodiments, the first mixing chamber solution has a different condition from the second mixing chamber solution, and the condition is selected from the group consisting of temperature, ionic strength, pH, solvent polarity, mixture of pure solvents, solution composition, sample concentration (e.g., the concentration of the diluted reactor liquid), illumination, and radiation. For example, the different condition can be ionic strength or pH. In various embodiments, each mixing chamber has a different condition from another mixing chamber.

In some cases, the detector detecting the property of the first mixing chamber solution, the second mixing chamber solution, or the third mixing chamber solution (when present) is a type selected from the group consisting of light scattering, ultraviolet/visible absorption, infrared absorption, refractometry, viscosity, conductivity, pH, polarimetry, turbidity, fluorescence, circular dichroism, Raman scattering, and birefringence.

In some embodiments, the chemical reactor comprises a polymerization reaction.

In various cases, the composition of at least one solvent is modified based on the property detected by at least one detector before the solvent is flowed into the mixing chamber.

Further aspects and advantages will be apparent to those of ordinary skill in the art from a review of the following detailed description, taken in conjunction with the drawings. While the devices and methods disclosed herein are susceptible of embodiments in various forms, the description hereafter includes specific embodiments with the understanding that the disclosure is illustrative, and is not intended to limit the invention to the specific embodiments described.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
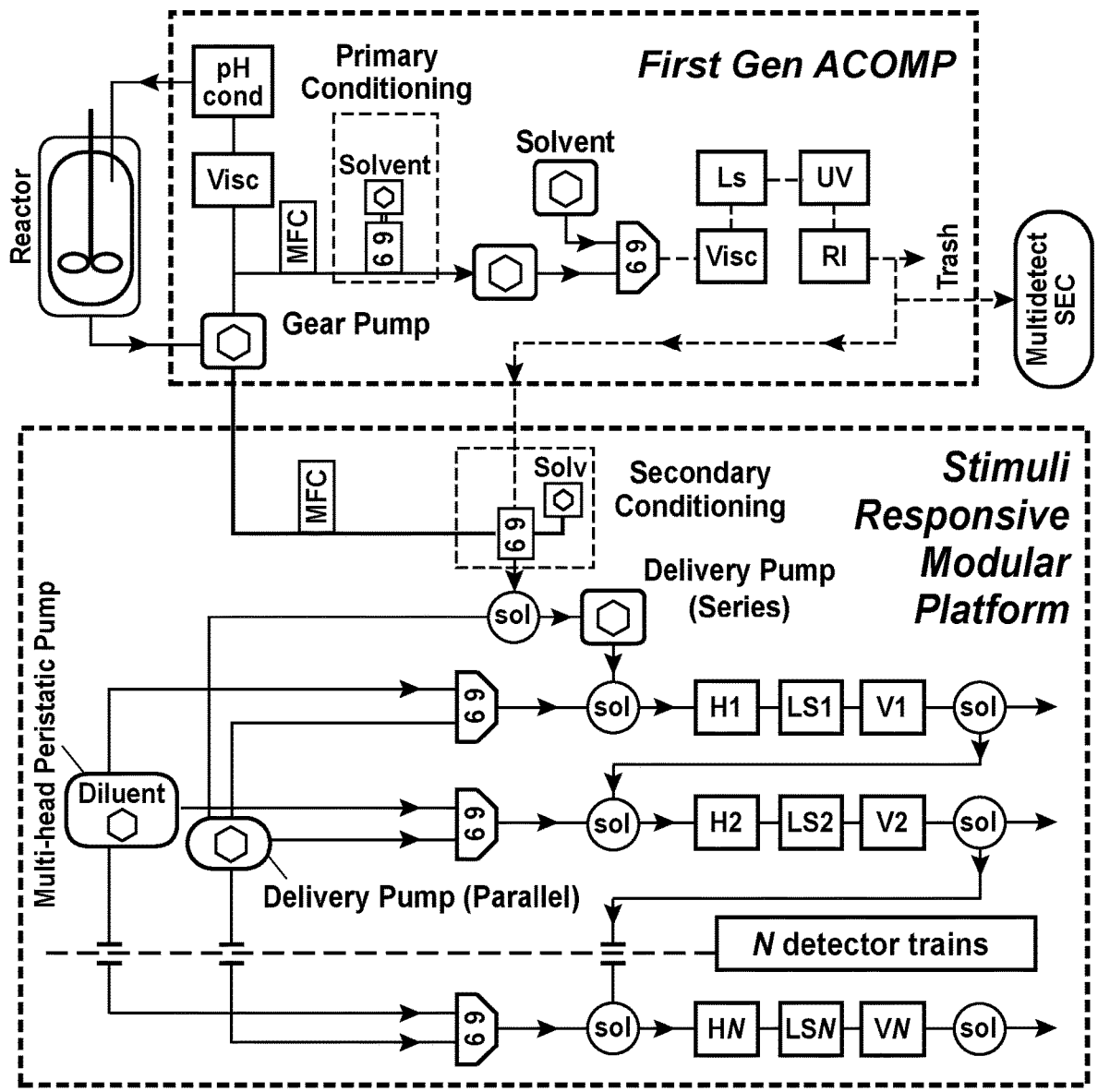
FIG. 1 shows a schematic of a First Generation ACOMP ("FGA") system that feeds into a Second Generation ACOMP ("SGA") system.

Disclosed herein are a device and method that allow for the continuous monitoring and control of a chemical reaction, such as a polymerization reaction, by altering and/or detecting the conditions of the reaction as a sampled portion of the reaction solution flows in a serial path. In particular, the present disclosure provides a device and methods for changing solution conditions of a liquid stream in serial flow in discrete increments, interposing one or more detectors in the serial flow path between the incremental changes to the solution. This allows the one or more measuring instruments between solution conditions to determine properties of the solution, including the state of polymers or colloids contained in the solution at each given solution condition. This is a far more concise, economical, practical, and efficient way of providing solutions of multiple conditions in a single serial flow, rather than using individual, parallel mixing stages to obtain multiple solution conditions for measurement.

The serial device and method disclosed herein are significantly less wasteful of sample, more economical, more efficient, and of higher performance than the known parallel device and method. In contrast to the parallel device, which needs one sample stream for each different solution condition (i.e., N sample streams are needed for N different solution conditions), the serial device uses only one sample stream, no matter how many different solutions conditions are present (i.e., 1 sample stream is needed for N different solution conditions). Therefore, the parallel flow device and method will consume N times more sample from the reactor than the serial device, making the parallel method much more wasteful. Furthermore, the parallel device and method require a separate solution delivery pump for each solution condition (i.e., N solution delivery pumps). In contrast, the serial device can use a single solution delivery pump that drives solutions through all N stages, making the serial device significantly more economical. Furthermore, there can potentially be N times more pump problems during an interval of operation time than for a single solution delivery pump over the same interval of operation, making the performance of the parallel method inferior to that of the serial device. Additionally, maintenance costs for N solution delivery pumps are likely to be N times higher than for a single solution delivery pump in the serial device.

An advantage of the present disclosure is that it allows the response and properties of polymers and/or colloids to be monitored simultaneously under different solution conditions during synthesis. Hence, the response of polymers to changing solution conditions such as but not limited to ionic strength, pH, surfactants, fluorescent dyes, temperature, and illumination, can be correlated to characteristics of the polymer or colloid at each instant of its synthesis. The results are both a better understanding of the physical and chemical processes controlling a polymer's or colloid's response to solution conditions and optimized synthetic processes. The present disclosure allows the industrial scale manufacturing of sophisticated polymers, including but not limited to, stimuli responsive polymers and colloids, which can currently be too challenging for optimization and scale-up.

The ACOMP system with the parallel flow design, as shown in FIG. 1, has a number of disadvantages that are improved upon with the serial flow design disclosed herein. For example, the reactor withdrawal rate is N times higher for parallel mode as compared to a serial mode, where N is the number of detection stages. The mixing system is more complex because each of the N stages requires separate dilution and mixing. Overall system complexity and cost is increased as it requires both serial and parallel flow paths and there is a need to toggle between serial and parallel modes. The system also wastes reactor liquid and dilution solvents when changing solution conditions incrementally between changes, such as changing pH, ionic strength, or surfactants.

The serial flow model disclosed herein offers many advantages over a parallel flow model and the combination serial/parallel flow model used in FIG. 1, including but not limited to, a simpler design, lower cost to build, less probability of operational and maintenance problems, less consumption of reactor liquid and solvents, and the ability to add different solvent components in successive stages—i.e., "online formulation." These advantages contribute to lower operational costs and efficiency gains of the ACOMP system.

However, in some instances the serial flow model is less optimal, because the solvent changes build off each previous change, so that many completely different solvent conditions (e.g. different solvents, same ionic strength but different salts) cannot be tested simultaneously. The following are examples of when the serial mode is less optimal: when it is desired to test the conformational properties of a polymer in different solvents that are compatible to some extent with the reactor liquid; and when the behavior of a polymer is to be tested with respect to different types of salts, surfactants, specific metal ions, different dyes, etc. Neither of these tests can be done in serial mode. Further, in some embodiments, the present disclosure is not needed if the non-equilibrium solution only requires measurement under a single solution condition.

The serial mode disclosed herein is particularly advantageous when the behavior of a polymer with respect to increasing ionic strength can be measured by incrementally increasing the ionic strength between mixing stages. This can be done in parallel mode but it is wasteful and inefficient. Further, 'online formulation', the effects of successively adding different solution components—e.g., surfactants, other polymer, salts, pH changes—can be done using the multiple stages in parallel, but by a much more wasteful and inefficient process of creating entire 'formulated reservoirs' for parallel stage dilutions. Further still, changes in factors not related to the solution are also best performed in serial mode, but do not require the solvent changing feature; e.g. changing temperature between stages, illumination or irradiation, including but not limited to ionizing radiation and ultrasound. While these changes could be done in parallel mode this would be highly inefficient and wasteful.

In some embodiments, the present invention can be used if the non-equilibrium solution needs to be measured under a variety of solution conditions at substantially the same time, where this latter phrase means the time needed for multiple measurements is much shorter than the time scale of the non-equilibrium process—e.g. if all such measurements at the different solution conditions could be made in under one minute and the non-equilibrium process involves changes that require tens of minutes or hours to occur, then these measurements would be at 'substantially the same time' with respect to any instantaneous non-equilibrium state of the solution. An example is free radical homo- and copolymerization reactions which typically last from tens of minutes to several hours. In general, there is a delay time between successive, serial detectors in any ACOMP system, or in any system with serial detectors, e.g. the use of light scattering, viscometric, refractive index, and ultraviolet/visible absorbance detectors in multi-detector gel permeation chromatography. The delay time depends on the 'dead volume' between detectors and the flow rate used. An example, not limiting, is where a flow rate is 2 ml/minute and there is 0.10 ml of dead volume between detectors. In this case there is a three second delay between detectors. For the present invention, as an example, not limiting, if N=8 stages and there are two detectors per stage (e.g. light scattering and viscosity) then there will be a delay of about 48 seconds from the first to last detector in the entire series. Most polymerization reactions take tens of minutes or hours and such a delay is normally deemed inconsequential. Furthermore, analysis software easily accounts for the delay between detectors when data are analyzed to compute properties of the polymers and/or colloids in the flowing stream. Hence, at any instant the device makes essentially simultaneous measurements on the same instantaneous sample under multiple different conditions.

As used herein, the term "adapted to contain" refers to the ability of an object to have, hold, or carry something within it, such as a liquid.

As used herein, the term "adapted to deliver" refers to the ability of an object to convey, carry, or transport something, such as a liquid to another object.

As used herein, the term "in communication with" refers to any form of interaction between two or more components, including mechanical, electrical, magnetic, and electromagnetic interaction. Two components may be connected to each other, even though they are not in direct contact with each other, and even though there may be intermediary devices between the two components.

As used herein, the term "in fluid communication with" refers to a route and/or system of routes for the flow of a fluid, the traveling and/or transporting of a fluid, and/or the general ability or capacity for fluid to flow between the parts, sections, or components under consideration.

Serial Flow Device

The serial flow device disclosed herein can be used to determine how polymers and colloids respond to varying solution conditions. Most polymers and colloids will respond in some way to changes in solution conditions. For example, polyelectrolyte chains can expand as ionic strength decreases, polyacids and polybases can undergo conformational changes as pH changes, and colloids can be made to coalesce as solution conditions change. A further focus within this category concerns the measurement of how stimuli responsive polymers ("SRP"), or 'smart polymers', respond to changing solution conditions, primarily during their synthesis. SRP are a relatively small category of polymers within the space of all polymers, but their development to provide functions, such as surface modifying materials, self-healing materials, and drug delivery agents, is of current intense interest. Some specific examples of SRP contemplated herein include, but are not limited to, _those that have lower critical solution temperatures, such as poly-N-isopropyl acrylamide (pNIPAM) and its copolymers; upper critical solution temperatures; cavitands; dendrimers; star-shaped polymers; block copolymers that can micellize and form supramolecular assemblies; cyclodextrins; _synthetic polymers hybridized to biological polymers, such as acrylates polymerized to polysaccharides, or polyethylene glycols grafted to proteins or polysaccharides; nanoparticles of silica; metals; insulators and semi-conductors, to which polymers are grafted. See, e.g., References 42-50.

Figure 2:
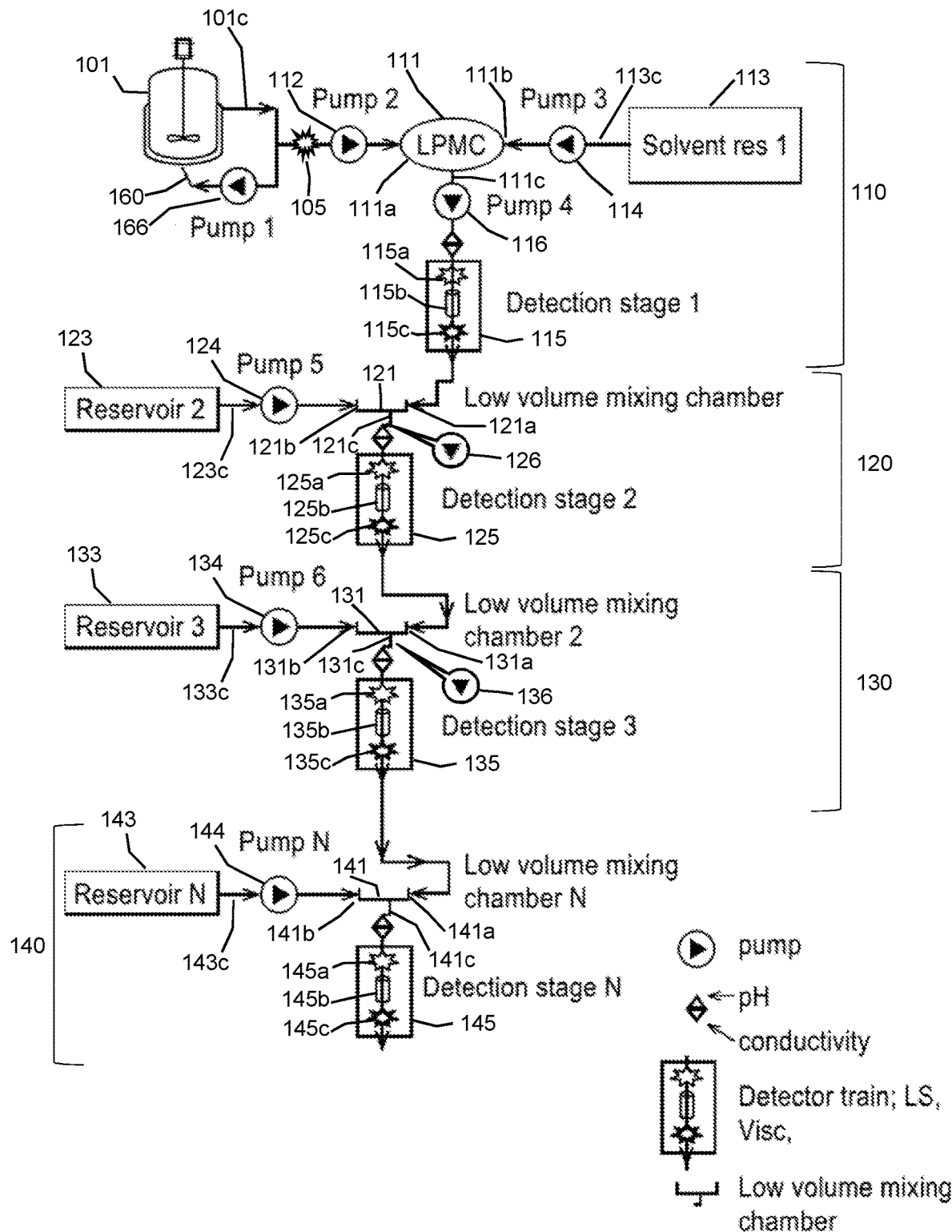
FIG. 2 shows an embodiment of the present disclosure as implemented.

FIG. 2 shows an embodiment of the present disclosure. The reactor has a recirculating loop driven by pump 1. The recirculating loop is optional in the devices disclosed herein. Pump 1 can be of the gear type, centrifugal, syringe, peristaltic, piston, slot, lobe, or other type. Pump 2 withdraws a small, continuous stream from the recirculation loop, typically in the range of 0.01 $cm^3$/min to 25 $cm^3$/min, depending on the volume of the reactor and the duration of the reaction, among other considerations. Pump 2 can be of any type well-suited to the viscosity of the reactor liquid, including a gear pump, piston pump, peristaltic pump, syringe pump, lobe pump, slot pump, Q-pump (Fluid Metering, Inc., Syosset, NY).

Pump 2 may in some instances be replaced by a mass flow controller which works off the pressure in the recirculation loop and automatically maintains the desired extraction flow rate. The metered flow of Pump 2 feeds into the mixing chamber, which is also fed via pump 3 from a solvent reservoir. The mixing chamber can be high pressure or low pressure. The task of pump 3 is merely to pump solvent at a controllable rate from the reservoir into the mixing chamber, and can hence be of a wide variety of pumps, including dosing pumps, peristaltic, and piston. Typical dilutions in the mixing chamber can run from less than 100% up to many thousand-fold. For example, if the reactor does not have a high concentration of monomers, and polymers it might suffice to provide a very low dilution, such as a factor of 50%. In the case of a dilute reactor liquid the first solvent dilution stage with the mixing chamber may be omitted and the withdrawn liquid may pass through the rest of the system, receiving incremental additions of liquid to change the solution condition at each subsequent stage. In the case of turbid reactor solutions, or where an extremely dilute solution is needed (e.g., for optical particle sizing) the dilution may be several thousand fold.

Pump 4 continuously withdraws the diluted content of the mixing chamber and pumps it through the remainder of the serial liquid flow path, including through all subsequent mixing stages. Flow rates for Pump 4 typically range from 0.2 to 5 ml/min, but may be slower or faster, depending on the context. After exiting from pump 4 this flowing liquid continues its serial path into a bank of detectors, detector stage 1. In the detector stage 1, pH and conductivity devices make measurements of the pH and conductivity of the flowing liquid. In the detector stage 1 the flowing liquid continues its serial path into a bank of other detectors, which makes characterizing measurements on the liquid. In one embodiment, the flowing stream contains one or more of monomers, polymers, simple electrolytes (e.g., salts), acid, base, surfactants, nanoparticles, proteins, polysaccharides, or other biological polymers, colloid particles, biological cells or cell fragments, organelles, micelles, aggregates, microgels, microcrystals, liposomes, vesicles, emulsions, small molecules, chelating agents, metal ions, and fluorescent dyes. The types of detectors used include one or more of the following: single or multi-angle total intensity light scattering, dynamic light scattering, Mie scattering, fluorescence, turbidity, viscosity, refractometer, polarimeter, circular dischroism, near or mid-infrared, and Raman detection. The types of polymer and colloid characteristics typically determined include weight average molecular weight, molecular weight distribution, intrinsic viscosity, conversion of monomers, conversion of comonomers, composition drift, instantaneous and average comonomer composition, polydispersity, optical activity, diffusion coefficients, virial and other interaction coefficients, particulate content, and ratios of fluorescence at different wavelengths. Such measurements can reveal many characteristics about the polymer or colloid including its ability to trap small molecules (such as drugs or fluorescent dyes), ability to form secondary and tertiary structures, optical activity, micellization, conformational changes, phase transitions (such as a lower critical solution temperature or upper solution critical temperature), degrees of branching, cross-linking, concentration dependent associations, aggregation, and nanostructuration.

After detection stage 1, pump 5 delivers a desired liquid from liquid reservoir 2 into the stream exiting detection stage 1 and mixing takes place in mixing chamber 1. The mixed liquid then flows through detection stage 2 where properties similar to those in detection stage 1 are measured. In one embodiment detection stage 2 contains the same components as detection stage 1. In another embodiment detection stage 2 contains any combination of stage 1 components and/or other components—i.e., it is not necessary that the different detection stages contain the same detectors.

After detection stage 2 the flowing liquid is mixed with a desired liquid—such as those of given pH, ionic strength, given concentration of surfactants, small molecules, or polymers or colloids, fluorescent dyes or labels, and drugs—from liquid reservoir 3 using pump 6, and this mixed liquid then flows through detection stage 3. The liquid addition and detection stages continue until the liquid exits from detection stage N. In some embodiments this liquid is led to waste, and in other embodiments it is injected into a chromatographic system (such as Gel Permeation Chromatography) with multi-detection or simply concentration detection. A system that connected a GPC system with automatic injection was presented recently is described in Reference 51. In other embodiments the liquid is saved in whole or in time-stamped aliquots for further analysis on remote instruments including gel permeation chromatography (also termed 'size exclusion chromatography'), NMR, mass spectrometry, Raman scattering, infra-red absorption, differential scanning calorimetry, rheometry, thermogravimetric analysis, and many other types of measurements Where a low pressure mixing chamber ("LPMC") is used, there is frequently a 'wasting stage'. That is, liquid can be pumped into the LPMC faster than it is pulled into the main exit stream. The excess in this case is removed, or siphoned, or 'wasted off'. For example, a 0.1 cm$^3$/min stream may be continuously extracted from the reactor and mixed in the LPMC with a flow of 1.9 cm$^3$/min from a solvent reservoir. The dilution is 20×. If only 0.5 ml/min of this mixed liquid is to be pumped through the serial stream by the solution delivery pump, the other 1.5 ml/min issuing from the LPMC, which is normally of fixed volume so that flow rate in is equal to flow rate out, is led off to waste or for solvent recovery (or other purposes) but does not form part of the principal stream forming the serial flow.

The mixing chamber disclosed herein can be a LPMC or a high pressure mixing chamber ("HPMC"). When a LPMC is used, a solution pump can be used to withdraw sample solution from the LPMC through the device to subsequent detectors and subsequent mixing chambers, if any. When a HPMC is used, the sample solution can flow through the detectors and subsequent mixing chambers without the need for an additional solution pump. Further, the volume of sample solution in a LPMC is often significantly higher than the volume present in an HPMC. For example, many millifluidic HPMCs have 10 microliter mixing volumes, whereas typical LPMC volume are 1 milliliter to 50 milliliters. Hence, HPMC can be preferred in some embodiment, but LPMCs can often find utility, usually only one or two per system.

Figure 3:
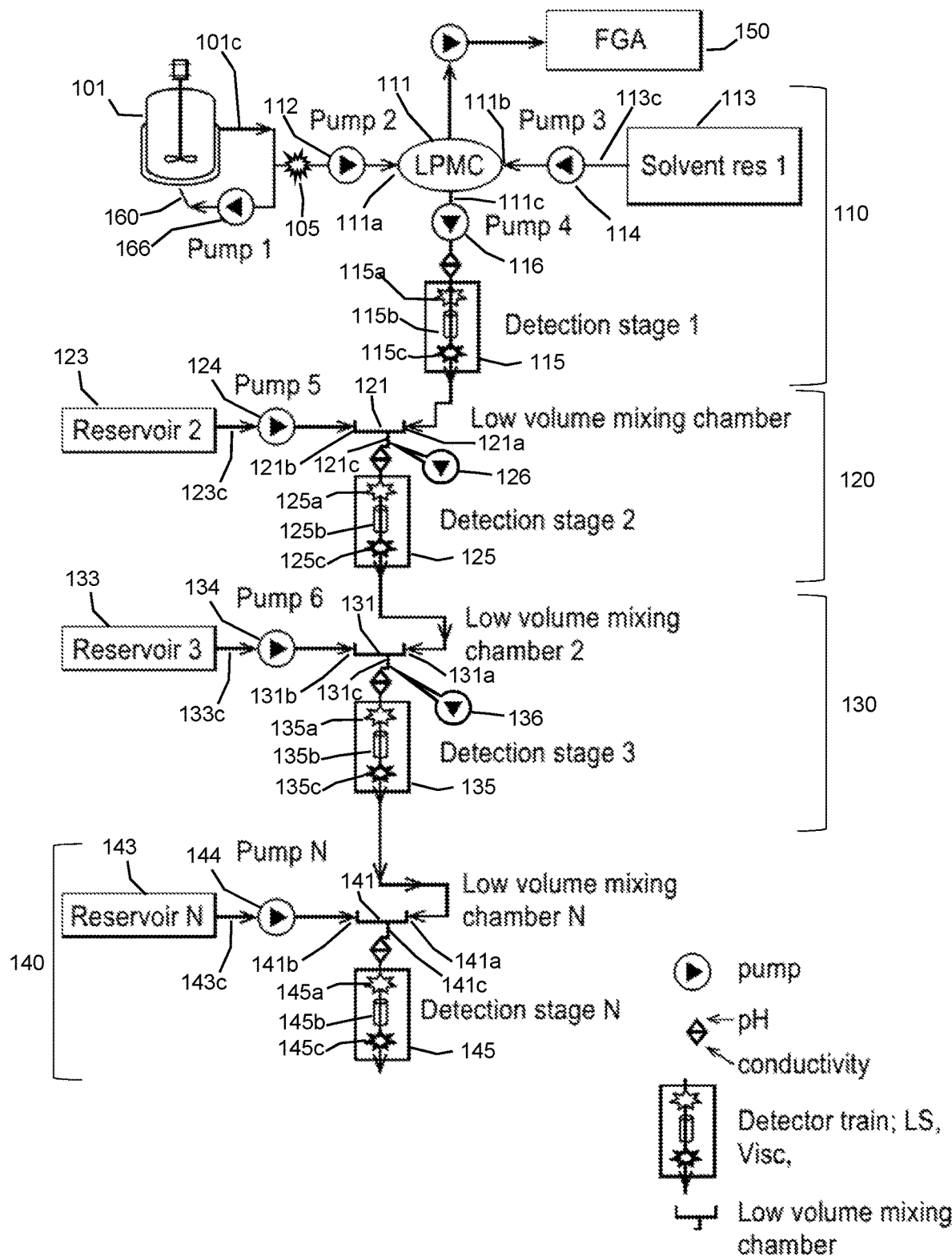
FIG. 3 shows an embodiment of the present disclosure, as implemented, wherein the device includes a separate extraction and dilution stage 150 directly out of the first mixing chamber which then goes to a first generation ACOMP for separate measurements. This can be desirable when the FGA measurements need to be made under different concentration and solution conditions than those available in the serial flow stream.

FIG. 3 shows an embodiment of the present disclosure, as implemented, wherein the device includes a separate extraction and dilution stage directly out of the first mixing chamber which then goes to a first generation ACOMP for separate measurements. This can be desirable when the FGA measurements need to be made under different concentration and solution conditions than those available in the serial flow stream.

In other embodiments, the device disclosed herein has one or more serial dilution stages. There is no fundamental limit to the number of stages, and instruments with more or less dilution stages can be constructed.

In various embodiments, the present disclosure has eight (8) serial dilution stages. In other embodiments the prevent invention provides automatic control of how solution conditions are determined in serial flow.

In some embodiments, the device disclosed herein includes (a) a sample reservoir (e.g., a chemical reactor or an injection loop) adapted to contain a sample;
(b) a first system that includes: (i) a first mixing chamber adapted to contain a first mixing chamber solution; (ii) a first sample pump adapted to deliver the sample from the sample reservoir into the first mixing chamber; (iii) a first solvent reservoir adapted to contain a first solvent; (iv) a first solvent pump adapted to deliver the first solvent from the first solvent reservoir into the first mixing chamber; and (v) a first detector in fluid communication with the first mixing chamber; and
(c) a second system serial to the first system, the second system including: (i) a second mixing chamber downstream of, and in fluid communication with, the first detector, and adapted to contain a second mixing chamber solution; (ii) a second solvent reservoir adapted to contain a second solvent; (iii) a second solvent pump adapted to deliver the second solvent from the second solvent reservoir into the second mixing chamber; and (iv) a second detector in fluid communication with the second mixing chamber.

In some embodiments, the device further includes a third system serial to the second system, the third system including: (i) a third mixing chamber downstream of, and in fluid communication with, the second detector, and adapted to contain a third mixing chamber solution; (ii) a third solvent reservoir adapted to contain a third solvent; (iii) a third solvent pump adapted to deliver the third solvent from the third solvent reservoir into the third mixing chamber; and (iv) a third detector in fluid communication with the third mixing chamber.

In some cases, the device can further include one or more additional systems in a serial path, each system including a mixing chamber, a solvent reservoir, a solvent pump, and at least one detector. For example, the device can include a total of two, three, four, five, six, seven, eight, nine, or ten systems. In some embodiments, the device can include more than ten systems. The number of systems included in the device depends on the particular application for which it is being used. There is no limit to the number of systems that the device can have in a serial path.

In various embodiments, the device further includes a recirculating loop that enables the sample flowing from the sample reservoir to be flowed back into the sample reservoir. In some embodiments, the device does not include a recirculating loop.

In some cases, the device further includes one or more additional detectors. In various cases, the one or more additional detector is positioned between the sample reservoir and the first mixing chamber, and is in fluid communication with the sample reservoir and the first mixing chamber. In some embodiments, the one or more additional detector is positioned downstream to, and in fluid communication with, the first mixing chamber, the second mixing chamber, or the third mixing chamber (when present). In some cases, the detectors present in a particular system are in communication with each other.

The detectors of the device can detect a property of the reaction sample. Examples of the detectors used to detect the property include, but are not limited to light scattering, ultraviolet/visible absorption, infrared absorption, refractometry, viscosity, conductivity, pH, polarimetry, turbidity, fluorescence, circular dichroism, Raman scattering, and birefringence. In some cases, none of the detectors present in the device detect the same property. In various cases, all of the detector present in the device detect the same property but under different conditions. In some embodiments, at least two of the detectors present in the device detect the same property.

In various embodiments, each system of the device includes at least two (e.g., 2, 3, or 4) detectors that operate at different conditions, while the solutions that they detect have the same composition. In these embodiments a sample solution that flows through the device can be split into a number of separate streams after leaving a mixing chamber, and each separate stream can flow to a separate detector to detect a property of the separate stream. The separate streams can then recombine after the detection step in a subsequent mixing chamber to continue a serial flow path. For example, pNIPAM and its copolymers undergo a lower critical solution temperature ("LCST") that depends on ionic strength, among other factors. In accordance with the present disclosure, a sample solution containing pNIPAM copolymers can be prepared in a mixing chamber of the device. The resulting mixing chamber solution that flows out of the mixing chamber can be split into two or more streams and delivered to two or more light scattering detectors, each at a different temperature, to enable the LCST to be determined under the particular solution condition and state of synthesis of the polymers. Subsequent mixing stages that change ionic strength can likewise have two or more light scattering detectors after them to determine the LCST under the corresponding ionic strength. Because the LCST at each particular instant of synthesis is being measured, a comprehensive diagram of LCST as a function of ionic strength and polymer characteristics such as composition and molar mass can be built up during the reaction.

The mixing chambers disclosed herein can be low pressure mixing chambers or high pressure mixing chambers. In some embodiments, at least one of the first mixing chamber and the second mixing chamber is a low pressure mixing chamber. In embodiments when a low pressure mixing chamber is used, a wasting stage can be present, as previously disclosed herein. In various embodiments, all of the mixing chambers are high pressure mixing chambers.

The device can include at least one additional sample pump that is adapted to deliver a mixing chamber solution from a mixing chamber to a detector. In various embodiments, the at least one additional sample pump is adapted to deliver the first mixing chamber solution from the first mixing chamber to the first detector, the second mixing chamber solution from the second mixing chamber to the second detector, or the third mixing chamber solution from the third mixing chamber to the third detector (when present). In some embodiments, the device includes a low pressure mixing chamber and at least one additional sample or solution pump. In various cases, the device includes only high pressure mixing chambers and no additional sample or solution pump.

In some cases, the device further includes a conditioning component positioned between a mixing chamber and a detector (e.g., between the first mixing chamber and the first detector, the second mixing chamber and the second detector, or the third mixing chamber and the third detector (when present)). The conditioning component can condition the first mixing chamber solution or the second mixing chamber solution to a pre-selected condition. In various cases, the device further includes a first conditioning component positioned between the first mixing chamber and the first detector that can condition the first mixing chamber solution, and a second conditioning component positioned between the second mixing chamber and the second detector that can condition the second mixing chamber solution. Conditioning can include, but is not limited to, filtration of the flowing solution by filters such as of the membrane, frit, disk, sintered metal, and other types, exhaling bubble to the atmosphere that may be caused by exothermic or other processes in the reactor, inverting the phase of reactor components, such as with surfactants, evaporating off monomers, and separating solution components according to density. In some cases it may be desired to eliminate ions, such as metal ions, from the serial flow, in which case conditioning can include the use of an electrode to attract and remove such ions from the flowing solution.

The sample reservoir can be any vessel that can contain a liquid to be delivered to the first detector, optionally through the first mixing chamber. For example, the sample reservoir can be a chemical reactor or an injection loop. In some embodiments, the sample reservoir is a chemical reactor. In these embodiments, the sample reservoir includes a chemical reaction, such as a polymerization reaction. In various embodiments, the sample reservoir is an injection loop, such as the sample loop and injector valve commonly found in chromatography apparatus, such as gel permeation chromatography (GPC) and size exclusion chromatography (SEC). The volume of sample in the loop injected into such systems is typically 0.01 $cm^3$ up to 1 $cm^3$. Therefore, an injection loop can be used as the sample reservoir, for example, in applications where a small volume of sample is to be injected into the serial device, and to be monitored under the N solution conditions provided in the serial path. Use of an injection loop is particularly advantageous when a certain chemical sample is hard to obtain or is expensive. For example, many new polymers, especially stimuli responsive polymers, are produced in small quantities, such as milligrams or tens of milligrams. A typical concentration in the detectors in the current serial flow device is 0.001 $g/cm^3$ to 0.010 $g/cm^3$. With a typical injection loop of 0.100 $cm^3$, it is possible to use as low as 0.1 milligram of chemical sample in 0.100 $cm^3$ of injected solution. Another field in which sample is very expensive is in the development of biologic drugs, such as therapeutic monoclonal antibodies and antiviral proteins. In such developments 1 milligram or a few tens of milligrams can involve months of labor to produce. The serial device would allow the behavior of these to be tested under a variety of solution conditions with a single injection.

In some cases the sample that flows through the device can include a component that includes, but is not limited to, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a chelating agent, a metal ion, a fluorescent dye, or combinations thereof. For example, the sample can include a polymer, a monomer, or combinations thereof.

In some embodiments, at least one of the solvents in a solvent reservoir is not identical to at least one (or not identical to any) other solvent present in the device (e.g., the third solvent is not identical to at least one of the first solvent or the second solvent). For example, two of the solvents present in the device can have different pH values and/or different ionic strengths. In some embodiments, the first solvent and the second solvent have different ionic strengths. In various cases, the first solvent and the second solvent have different pH values.

In various embodiments, at least one of the solvents present in the device includes a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a fluorescent dye, a chelating agent, a metal ion, or combinations thereof. For example, the first solvent and/or the second solvent can include a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a chelating agent, a metal ion, a fluorescent dye, or combinations thereof.

In some cases, the device is in fluid communication with a First Generation Automatic Continuous Online Monitoring of Polymerization Reactions ("FGA") system. In various cases, the FGA system is in fluid communication with a mixing chamber. Connecting a FGA to the device disclosed herein so that a sample stream can be separately extracted from the device and flowed into the FGA allows the detection of, e.g., conformational properties of a polymer in different solvents that are compatible with the reactor liquid, and when the effect of different types of salts, surfactants, specific metal ions, different dyes, etc., are desired.

FIGS. 2 and 3 show specific embodiments of the present disclosure in which the device 100 disclosed herein includes: a sample reservoir 101 adapted to contain a sample, the sample reservoir 101 comprising a sample reservoir outlet conduit 101c; a first system 110; a second system 120; a third system 130; and an N system 140. Each system comprises a detection stage (i.e., a detector train) designated as 115, 125, 135, and 145. FIGS. 2 and 3 depict embodiments of the disclosure in which each detector train 115, 125, 135, and 145 comprises three detectors designated as 115a, 115b, and 115c for the first system 110; 125a, 125b, and 125c for the second system 120; 135a, 135b, and 135c for the third system 130; and 145a, 145b, and 145c for the N system 140.

As shown in FIGS. 2 and 3, the first system 110 can comprise: (i) a first mixing chamber 111 adapted to contain a first mixing chamber solution, the first mixing chamber comprising a sample inlet 111a, a first solvent inlet 111b, and a first mixing chamber outlet conduit 111c; (ii) a first sample pump 112 in fluid communication with the sample reservoir 101 and the first mixing chamber 111, the first sample pump 112 adapted to deliver the sample from the sample reservoir 101 through the sample reservoir outlet conduit 101c into the sample inlet 111a of the first mixing chamber 111; (iii) a first solvent reservoir 113 adapted to contain a first solvent, the first solvent reservoir 113 comprising a first solvent reservoir outlet conduit 113c; (iv) a first solvent pump 114 in fluid communication with the first solvent reservoir 113 and the first mixing chamber 111, the first solvent pump 114 adapted to deliver the first solvent from the first solvent reservoir 113 though the first solvent reservoir outlet conduit 113c into the first solvent inlet 111b of the first mixing chamber 111; and (v) a first detector 115a in fluid communication with the first mixing chamber 111.

As shown in FIGS. 2 and 3, the second system 120 is serial to, and downstream of, the first system 110, and can comprise: (i) a second mixing chamber 121 adapted to contain a second mixing chamber solution, the second mixing chamber 121 comprising a second mixing chamber inlet 121a, a second solvent inlet 121b, and a second mixing chamber outlet conduit 121c, the second mixing chamber 121 in fluid communication with the first detector 115a; (ii) a second solvent reservoir 123 adapted to contain a second solvent, the second solvent reservoir 123 comprising a second solvent reservoir outlet conduit 123c; (iii) a second solvent pump 124 in fluid communication with the second solvent reservoir 123 and the second mixing chamber 121, the second solvent pump 124 adapted to deliver the second solvent from the second solvent reservoir 123 through the second solvent reservoir outlet conduit 123c into the second solvent inlet 121b of the second mixing chamber 121; and (iv) a second detector 125a in fluid communication with the second mixing chamber 121.

As shown in FIGS. 2 and 3, the third system 130 is serial to, and downstream of, the second system 120 and can comprise: (i) a third mixing chamber 131 downstream of and adapted to contain a third mixing chamber solution, the third mixing chamber 131 comprising a third mixing chamber inlet 131a, a third solvent inlet 131b, and a third mixing chamber outlet conduit 131c, the third mixing chamber in fluid communication with the second detector 125; (ii) a third solvent reservoir 133 adapted to contain a third solvent, the third solvent reservoir 133 comprising a third solvent reservoir outlet conduit 133c; (iii) a third solvent pump 134 in fluid communication with the third solvent reservoir 133 and the third mixing chamber 131, the third solvent pump 134 adapted to deliver the third solvent from the third solvent reservoir 133 through the third solvent reservoir outlet conduit 133c into the third solvent inlet 131b of the third mixing chamber 131; and (iv) a third detector 135a in fluid communication with the third mixing chamber 131.

As shown in FIGS. 2 and 3, the device 100 can further include additional systems, N systems serial to and downstream of the third system. For example, the device 100 can include a fourth system 140 serial to, and downstream of, the third system 130 comprising: (i) a fourth mixing chamber 141 downstream of and adapted to contain a fourth mixing chamber solution, the fourth mixing chamber 141 comprising a fourth mixing chamber inlet 141a, a fourth solvent inlet 141b, and a fourth mixing chamber outlet conduit 141c, the fourth mixing chamber in fluid communication with the third detector 135a; (ii) a fourth solvent reservoir 143 adapted to contain a fourth solvent, the fourth solvent reservoir 143 comprising a fourth solvent reservoir outlet conduit 143c; (iii) a fourth solvent pump 144 in fluid communication with the fourth solvent reservoir 143 and the fourth mixing chamber 141, the fourth solvent pump 144 adapted to deliver the fourth solvent from the fourth solvent reservoir 143 through the fourth solvent reservoir outlet conduit 143c into the fourth solvent inlet 141b of the fourth mixing chamber 141; and (iv) a fourth detector 145a in fluid communication with the fourth mixing chamber 141.

In embodiments, the device 100 further comprises: (i) a sample detector 105 in fluid communication with the sample reservoir 101, and in fluid communication with the first mixing chamber 111, wherein the sample detector 105 is configured to detect a property of the sample; (ii) a first system additional detector 115b positioned between the first detector 115a and the second mixing chamber 121, the first system additional detector 115b in fluid communication with the first detector 115a, and in fluid communication with the second mixing chamber 121; (iii) a second system additional detector 125b positioned between the second detector 125a and the third mixing chamber 131, the second system additional detector 125b in fluid communication with the second detector 125a, and in fluid communication with the third mixing chamber 131; or (iv) a combination thereof.

In embodiments, the device 100 comprises a first system additional detector 115b and a second system additional detector 125b. In embodiments, the first detector 115a and the first system additional detectors 115b detect the same property under different conditions, the second detector 125a and the second system additional detector 125b detect the same property under different conditions, or a combination thereof.

In embodiments, the device 100 further comprises: (i) a first system mixing chamber pump 116 in fluid communication with the first mixing chamber 111 and the first detector 115a, the first system mixing chamber pump 116 adapted to deliver the first mixing chamber solution from the first mixing chamber outlet conduit 111c of the first mixing chamber 111 to the first detector inlet of the first detector 115a; (ii) a second system mixing chamber pump 126 in fluid communication with the second mixing chamber 121 and the second detector 125a, the second system mixing chamber pump 126 adapted to deliver the second mixing chamber solution from the second mixing chamber outlet conduit 121c of the second mixing chamber 121 to the second detector inlet of the second detector 125a; (iii) or a combination thereof.

In embodiments, the device 100 further comprises a third system mixing chamber pump 136 in fluid communication with the third mixing chamber 131 and the third detector 135a the third system mixing chamber pump 136 adapted to deliver the third mixing chamber solution from the third mixing chamber outlet conduit 131c of the third mixing chamber 131 to the third detector inlet of the third detector 135a.

In embodiments, the sample reservoir 101 is a chemical reactor comprising a recirculation loop 160, and the first sample pump 105 is adapted to withdraw a small portion from the recirculation loop 160 as the sample delivered into the first mixing chamber 111.

Methods

Also disclosed herein is a method for monitoring or controlling a chemical reaction, such as a polymerization reaction. This method includes (a) flowing a sample from a sample reservoir into a first mixing chamber; (b) flowing a first solvent into the first mixing chamber; (c) mixing the sample and the first solvent to form a first mixing chamber solution; (d) flowing the first mixing chamber solution through a first detector to detect a property of the first mixing chamber solution; (e) flowing the first mixing chamber solution from the first detector to a second mixing chamber; (f) flowing a second solvent into the second mixing chamber, wherein the second solvent is nonidentical to the first solvent; (g) mixing the first mixing chamber solution and the second solvent to form a second mixing chamber solution; and (h) flowing the second mixing chamber solution through a second detector to detect a property of the second mixing chamber solution. The method further includes changing the conditions of the reaction in response to the multiple measurements made on the flowing sample. Such changes in reaction conditions can include, but are not limited to, reaction temperature, rate of stirring, addition of reagents such as, but not limited to, monomers, initiators, catalysts, quenching agents, branching agents, air, and other gases, small molecules such as salts.

In some embodiments, the method further includes flowing the sample from the sample reservoir to a detector prior to flowing the sample into the first mixing chamber. In these cases, the sample is dilute enough for its intended application and does not need to be mixed with a solvent before a property of the sample can be detected.

The method disclosed herein can further include additional steps wherein additional solvents (e.g., a third solvent, a fourth solvent, a fifth solvent, a sixth solvent, a seventh solvent, an eighth solvent) are serially introduced to the reaction solution and a property of the reaction solution is detected after each addition. In some embodiments, for example, the method further includes (i) flowing the second mixing chamber solution from the second detector to a third mixing chamber; (j) flowing a third solvent into the third mixing chamber; (k) mixing the second mixing chamber solution and the third solvent to form a third mixing chamber solution; and (l) flowing the third mixing chamber solution through a third detector to detect a property of the third mixing chamber solution. The number of systems through which the sample solution is flowed through depends on the particular application for which the method is being practiced. There is no limit to the number of mixing chambers and solution conditions through which a sample solution can be flowed in a serial path.

In some cases, the method includes flowing at least one of the first mixing chamber solution, the second mixing chamber solution, or the third mixing chamber solution (when present) through one or more additional detectors. For example, the first mixing chamber solution, the second mixing chamber solution, or the third mixing chamber solution (when present) can each flow through at least two detectors, as previously described herein. In various cases, the at least two detectors detect the same property under different conditions (e.g., different temperatures under the same solution conditions).

In some embodiments, the method further includes flowing a mixing chamber solution (e.g., a first mixing chamber solution, a second mixing chamber solution, a third mixing chamber solution (when present)) to a FGA, as previously described herein.

In some embodiments, the method further includes conditioning a mixing chamber solution prior to flowing the mixing chamber solution to a detector. For example, the method can include conditioning at least one of the first mixing chamber solution, the second mixing chamber solution, or the third mixing chamber solution (when present) prior to flowing through the first detector, the second detector, or the third detector, respectively.

In some cases, the mixing steps of the method can occur at low pressure or high pressure. For example, at least one of the mixing steps (c), (g), and (k) (when present) occurs at low pressure. In various cases, each of the mixing steps (c), (g), and (k) occurs at high pressure In some embodiments, the sample from the chemical reactor includes a molecule or additive, such as a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a chelating agent, a metal ion, a fluorescent dye, or combinations thereof. For example, the sample from the chemical reactor can include a polymer, a monomer, or a combination thereof.

In various cases, at least one of the first solvent or the second solvent includes a polymer, a monomer, a salt, an acid, a base, a surfactant, a nanoparticle, a protein, a polysaccharide, a colloid, a cell or fragment thereof, an organelle, a micelle, an aggregate, a microgel, a microcrystal, a liposome, a vesicle, an emulsion, a small molecule, a chelating agent, a metal ion, a fluorescent dye, or combinations thereof.

In some embodiments, at least two of the mixing chamber solutions have different conditions from each other. For example, the first mixing chamber solution can have a different condition from the second mixing chamber solution. In some cases, the different condition can be selected from the group consisting of temperature, ionic strength, pH, solvent polarity, mixture of pure solvents, solution composition, sample concentration (e.g., the concentration of the diluted reactor fluid), illumination, and radiation. For example, the different condition can be ionic strength or pH. In various embodiments, each mixing chamber has a different condition from another mixing chamber.

In some cases, each detector that detects a property is a type selected from the group consisting of light scattering, ultraviolet/visible absorption, infrared absorption, refractometry, viscosity, conductivity, pH, polarimetry, turbidity, fluorescence, circular dichroism, Raman scattering, and birefringence.

In some cases, the chemical reactor comprises a polymerization reaction. In various embodiments, the chemical reaction comprises a polymer modification reaction (e.g., alkylation, carboxylation, sulfation, quaternization, hydroxylation, amination, PEGylation, and phosphorylation).

In various cases, method further includes modifying the composition of at least one solvent, based on the property detected by at least one detector, before the solvent is flowed into the mixing chamber. Therefore, the method provided therein allows the control of a reaction, such as a polymerization reaction.

Applications

In some embodiments, the device and methods disclosed herein are useful for monitoring the physical and chemical changes of stimuli response polymers ("SRPs") (i.e., smart polymers) when they are exposed to a stimulus (e.g., temperature, humidity, pH, light, electrical field, magnetic field, another molecule, changes in their own concentration). SRP's are useful for a number applications such as, for example, sensing, encapsulation and release of agents, viscosity control, micropatterning, medical applications (e.g., as bioconjugated polymers), self-healing, photosensitivity, electrical properties for optics and electronics, nanowires, and photovoltaics. See References 1-8.

The device and methods disclosed herein allow SRP's to be 'fine-tuned' to have well-behaved stimuli responsiveness, interaction properties, and specific phase behavior. Changes of conditions such as, but not limited to, pH, ionic strength, ions, solvent polarity, surfactant content, specific small molecules, changes in SRP concentration (e.g., the SRP can act as stimuli to each other) and other polymers are considered 'stimuli' and SRPs can respond in numerous ways, including but not limited to, phase changes, micellization, drug entrapment and release. The device and methods disclosed herein allow any of these stimuli to be introduced to an SRP in any desired amount and combination as the serial flow progresses through the N stages, with detection occurring at each of the N stages which reveals if and how the polymers respond to these stimuli at each stage.

In contrast to the devices and methods described herein, most methods for relating polymer characteristics to their stimuli responsiveness are time-consuming and inefficient. These methods typically involve synthesizing a series of end-products or aliquots (e.g. Chemspeed, Symyx) and then serially characterizing the end-products or aliquots. End-product preparation alone can be lengthy, requiring steps such as precipitation, drying, and re-dissolution. Post-synthetic end-product analyses with methods such as size exclusion chromatography (SEC) and NMR yield little information on how polymer characteristics evolve during synthesis, nor is there any opportunity for reaction control.

The device and methods disclosed herein also are useful for polymers that are not generally considered stimuli responsive. Research, development, optimization, and manufacturing for many ordinary polymers and natural product polymers can benefit from the present disclosure. For example, during an ordinary functionalization reaction—e.g., one that converts an electrically neutral polymer into an electrically charged polymer, or polyelectrolyte—many properties of the molecule can change—e.g., its intrinsic viscosity, static and dynamic dimensions, excluded volume, interactions with other species. The present disclosure in this case allows the degree of conversion to be assessed continuously and how the polymers at each moment of conversion respond to the N different solution conditions in the serial flow. An example, not limiting, is the treatment of neutral polyacrylamide with sodium hydroxide (NaOH) to form negatively charged carboxylate groups on the polymer backbone. With the present disclosure, the polymer is exposed to N different solutions conditions, for example, N different ionic strength conditions (e.g., using NaCl at concentrations ranging from 0 molar to 0.5M), for which the intrinsic viscosity, dimensions, and excluded volume (e.g. measured in terms of virial coefficients $A_2$, $A_3$) are measured at each stage. This provides a map of the polymer's most important properties under various conditions, at each instant of its synthesis. The FGA, even without the present disclosure, provides complete measurements and analysis from its detectors every second, which rate can be increased or decreased according to the time scale of a complete reaction or process. An example, not limiting, where this type of conversion from neutral polymer to polyelectrolyte for polyacrylamide and NaOH was monitored by FGA, where only a single solution condition and single detection stage is described. See Reference 1.

There also are many other polymer modification reactions that could be better understood and optimized by using the device and methods disclosed herein during the modification reactions. These include, but are not limited to, alkylation, carboxylation, sulfation, quaternization, hydroxylation, amination, PEGylation, and phosphorylation. Where polybases and polyacids are formed, pH sensitivity can be tested in the serial flow stages.

The present disclosure can also be used during synthetic reactions not involving modifications of polymeric products. For example, not limiting, polyelectrolytes can be synthesized in stepwise and chain growth reactions and the present invention allows their polyelectrolyte behavior to be mapped under N solution conditions at each instant of their synthesis, so that the relationship between such properties as polyelectrolyte linear charge density and molecular weight, and varying solution conditions is revealed. More advanced forms of polymerization, such as controlled radical polymerization (e.g., ATRP, NMP, ROMP, RAFT) allow for polymer growth in a highly controlled fashion. The present invention will likewise yield information of the polymers under different solution conditions at each stage of their synthesis.

Many of the ordinary polymers and SRPs involve two or more monomers in their synthesis, and are termed 'copolymers'. Additional uses for the device and methods disclosed herein for copolymers, beyond those implicated in its use for SRP and ordinary polymers, include but are not limited to the monitoring of solution conditions on random and block copolymers. In the case of random copolymers, the solubility, dimensions, interaction with other molecules and polymers, etc. are often very dependent on the ratio of the comonomers in the copolymer chains. For example, if vinylpyrrolidone is copolymerized with polyquaternium-11, then the solubility in aqueous solution is a strong function of both copolymer composition and solution ionic strength. The present invention allows the behavior of the copolymer population to be monitored under N different solution conditions at each instant of their synthesis so that the relationship between solution behavior and copolymer composition and molecular weight is revealed. Similarly, block copolymers can acquire the ability to form micelles and other nano- and microstructures whose properties depend both on relative block lengths and composition in the copolymer and on the solution conditions. Hence, the present disclosure reveals the relationship between block copolymer structure and composition and its solution behavior.

Another class of materials that the present invention can be applied to is nanoparticles, including nanoparticles that are hybrids of solid or hollow nanoparticles and attached polymers. In the latter case the polymers are attached to nanoparticles or grown off the surface of the nanoparticles. The nanoparticles can be of a wide variety of material, such as but not limited to silica, gold or other metals, carbon nanotubes, clay and other minerals, viruses, bacteria, other microbes, and cells and cell organelles. The polymers that can be hybridized to the particles include virtually all polymers. The uses of nanoparticles and nanoparticle hybrids include but are not limited to drug encapsulation and release, antimicrobial agents, antibiotics and other agents useful in nanomedicine, entrapment of oil for oil spill remediation, and as coatings for optical, electronic, and mechanical systems, including anti-fouling agents for marine applications. The N stages of the present disclosure can be used to test the ability of the nanoparticles or hybrid nanoparticle/polymer systems to encapsulate agents, test stability, monitor aggregation, and other responses to N solution conditions at each instant of synthesis and processing. This will lead to better understanding of the properties of the particles and the relationship to their behavior and the optimization of synthesis and enablement of efficient manufacturing.

Yet another application of the present disclosure is the continuous titration of a solution. Many materials in solution respond differently to changes in solution conditions, such as, but not limited to, pH, ionic strength, presence of specific ions, small molecules, polarity, and surfactants. Providing continuous 'titration' of a solution to bring it from one state to another, e.g. from one pH to another, is common practice, whereas adding a given amount of a material, such as an acid, to change solution conditions is another common method. An existing method, such as Automatic Continuous Mixing (ACM), (see References 2-3), can provide the ability to change solution conditions along multiple paths in a space spanned by the composition of all agents in solution in a programmed way, either continuously or in steps.

Embodiments

In one embodiment, the device and methods disclosed here can be used to monitor the lower critical solution temperature ("LCST") of a copolymer. For example, the LCST of N-isopropyl acrylamide ("NIPAM") and another monomer (e.g. styrene sulfonate) can be monitored according to chain length and composition. Eight initial temperatures may be chosen, ranging from 15° C. to 90° C. There can be a light scattering detector at each serial stage, which can detect when the LCST is reached, which is manifested by a sharp increase in scattering. If, during the synthesis, there is no LCST over a part of the chosen range and LCST is clustered in a certain temperature range, a controller can shift the temperatures of the range not revealing the LCST to be more tightly clustered around the range where LCST is found. This will yield more relevant data and precision in the determination of LCST as a function of composition, molecular weight or other properties during synthesis. Also, since LCST of p-NIPAM and its copolymers is sensitive to ionic strength, at least one stage can also include a change in ionic strength, instead of, or in addition to temperature changes. An algorithm can likewise be found that adjusts the ionic strength range to that causing the greatest LCST effects. In some embodiments automatic controllers of temperature and pump flow rates are used to achieve changes in both temperature and ionic strength. The pumps used in the device offer features for external control, usually over a USB connection, Ethernet, etc.

In another embodiment, the device and methods disclosed herein can be used to find the optimal pH for the synthesis of a polymer. For example, if a certain polymer forms aggregates over a certain range of pH, the device disclosed herein can be used to narrow in on the most effective pH range during synthesis, and the pump rates for solution condition changing of the device can be adjusted for any number of desired stages to fall in the most effective range.

The device disclosed herein also can be used to modify the ionic environment of a pH-sensitive polymer during its synthesis, as exemplified in Table 1, below. The main stream flow rate of stage #n is that which flows through the detector train of stage #n, which is composed of the main stream rate of the previous pump plus the reservoir flow rate of stage #n. Table 1 shows how ionic strength can be varied from 0 to 651 mM (0.651M) ionic strength. Any desired electrolytes can be used, such as, but not limited to, NaCl, KCl, $MgCl_2$, and $MgSO_4$. The dilution of the sample stream is very low in the first five stages, amounting to 4% by the end of stage 5. As dilution is increased to achieve high ionic strength, the final stage has a 19% dilution. These dilutions are small and well known, so that any needed corrections in making calculations based on detector measurements can be made; for example, the polymer concentration needed to make molecular weight and intrinsic viscosity computations can be taken into account at each stage.

TABLE 1

Scheme for changing ionic strength for an 8 stage embodiment of the invention

| Stage # | Main stream flow rate ($cm^3$/min) | Main stream rate in ($cm^3$/min) | Reservoir flow rate ($cm^3$/min) | Reservoir ionic strength (mM) | Main stream ionic strength (mM) |
|---|---|---|---|---|---|
| 1 | 1.0 | 0.1 | 1.9 | 0 | 0 |
| 2 | 1.01 | 1.0 | 0.01 | 10 | 0.1 |
| 3 | 1.02 | 1.01 | 0.01 | 100 | 1.1 |
| 4 | 1.03 | 1.02 | 0.01 | 1000 | 11.1 |
| 5 | 1.04 | 1.03 | 0.01 | 4000 | 51.1 |
| 6 | 1.09 | 1.04 | 0.05 | 4000 | 251.1 |
| 7 | 1.14 | 1.09 | 0.05 | 4000 | 451.1 |
| 8 | 1.19 | 1.14 | 0.05 | 4000 | 651.1 |

The device disclosed herein also can be used in solution condition environments where the pH, rather than ionic strength, is changed in stages as exemplified in Table 2 below. Table 2 shows how pH can be reduced from 7 to 2.42 in eight (8) stages. In some embodiments, the pH is raised and then lowered in successive stages, and vice versa. In some embodiments a buffer is used, and the ionic strength and pH conditions are changed in successive stages. Any desired acids or bases can be used, including HCl, HF, $H_2SO_4$, NaOH, and $NH_4OH$.

TABLE 2

Scheme for changing pH in increments from pH = 7 to pH = 2.42, for an 8 stage embodiment of the invention.

| Stage # | Main Flow | Main Flow Intro | Dilution Flow Intro | [H+] | Reservoir pH | pH, main |
|---|---|---|---|---|---|---|
| 1 | 1 | 0.1 | 1.9 | $1.00 \times 10^7$ | 7 | 7.00 |
| 2 | 1.01 | 1 | 0.01 | $1.09 \times 10^6$ | 4 | 5.96 |
| 3 | 1.02 | 1.01 | 0.01 | $4.19 \times 10^6$ | 3.5 | 5.38 |
| 4 | 1.03 | 1.02 | 0.01 | $1.39 \times 10^5$ | 3 | 4.86 |
| 5 | 1.04 | 1.03 | 0.01 | $2.91 \times 10^5$ | 2.8 | 4.54 |
| 6 | 1.05 | 1.04 | 0.01 | $5.93 \times 10^5$ | 2.5 | 4.23 |
| 7 | 1.06 | 1.05 | 0.01 | $1.54 \times 10^4$ | 2 | 3.81 |
| 8 | 1.09 | 1.05 | 0.04 | $3.82 \times 10^3$ | 1 | 2.42 |

In some embodiments both pH and ionic strength are changed in the various serial stages, as well as the nature of the electrolytes, acids, bases, and buffering and excipients (e.g. TRIS, guanidine hydrochloride, arginine, polysorbate) materials used.

In various embodiments the present disclosure is used to characterize smart polymers (SRPs) during synthesis and determine how these respond to changing solution conditions during synthesis. Using the ACOMP and SGA platforms, the present invention allows, in a single experiment, the quantitative monitoring of how SRPs respond to changes in its solution environment.

In some cases the present disclosure is used to test the characteristics of nanoparticles and hybrid nanoparticle/polymer systems, such as their ability to encapsulate agents, test stability, monitor aggregation, and other responses to N solution conditions at each instant of synthesis and processing.

EXAMPLES

The following examples are provided for illustration and are not intended to limit the scope of the invention
Example: Monitoring and Controlling the Copolymerization of Acrylamide and Styrene Sulfonate A prototype of the invention was designed and built using the concepts disclosed herein, such as those embodied in FIG. 2. Seven stages for the device were built, each with a custom-built single capillary viscometer and a custom-built 90° light scattering flow cell. The seven viscometers were constructed from Validyne (P55D-1-K-1-28-S-4) differential pressure transducers with 'T'-fittings provided to join each end of a flow capillary to the high and low pressure sides of the pressure transducer. The pressure difference signal was proportional to voltage, which was provided to an analog/digital converter, which was connected to a computer, and any desired sample rate, such as 2 Hz, could be used. This type of viscometer has been previously described. See Reference 39.

The seven light scattering flow cells were constructed out of aluminum, with 5 mm central bores and a straight flow path. Illumination of the sample volume through windows in the cell was provided by a 35 mW LaserMax diode laser operating at a vacuum wavelength of 660 nm at vertically polarized incidence. Each cell had its own 35 mW laser. A fiber optic was mounted flush with the internal bore of the cell via a hole drilled for this purpose and a liquid chromatography ferrule to secure it in place. The fiber optic from each cell gathers scattered light and transmits it to a charge coupled device (CCD) camera (Mightex Corp., Model TCE-1304-U). The CCD sends the scattered intensity data to a computer via a USB connection at any desired sampling rate, such as 2 Hz.

Two four-headed syringe pumps (Nexus 6000) were used to accommodate six syringes (three syringes in each pump), each of which was filled with a desired solution. The contents of the syringes can be injected at any desired flow rate into the successive stages of the device. In these experiments, each syringe had a different concentration of NaCl to provide ionic strength ("IS") increasing after each stage. Table 3 shows the solution conditions in each stage. As used herein ionic strength ("IS") is defined as $$IS = \frac{1}{2}\sum_{i=A}^{Y} z_i^2 [i] \quad (1)$$

where is the molar concentration of each ion in Moles/m³, $z_i$ is the number of elementary charges per ion and y is the number of ions that the parent salt dissolves into. For NaCl y=2 and $z_i^2$=1 for Na⁺ and Cl⁻.

Table 3, below, shows the reservoir ionic strength (i.e. [NaCl]) of 20 mL syringes (diameter 1.9 cm) used with the multi-head syringe pump, the injection rate of each stage, the resulting net ionic strength in each stage, and the dilution factor at each stage from the original concentration flowing into the detector train, assigned the dilution factor of 1.

TABLE 3

| Channel Number | [NaCl], reservoir | Injection rate (ml/min) | Ionic strength in flow | Sample flow rate (ml/min) | Dilution factor |
|---|---|---|---|---|---|
| 1 | 0 | 0 | 0 | 1 | 1 |
| 2 | 2 | 0.05 | 0.095238 | 1.05 | 0.952381 |
| 3 | 20 | 0.05 | 1 | 1.1 | 0.909091 |
| 4 | 200 | 0.05 | 9.652174 | 1.15 | 0.869565 |
| 5 | 1000 | 0.05 | 50.91667 | 1.2 | 0.833333 |
| 6 | 2000 | 0.05 | 128.88 | 1.25 | 0.8 |
| 7 | 5000 | 0.05 | 316.2308 | 1.3 | 0.769231 |

Figure 4:
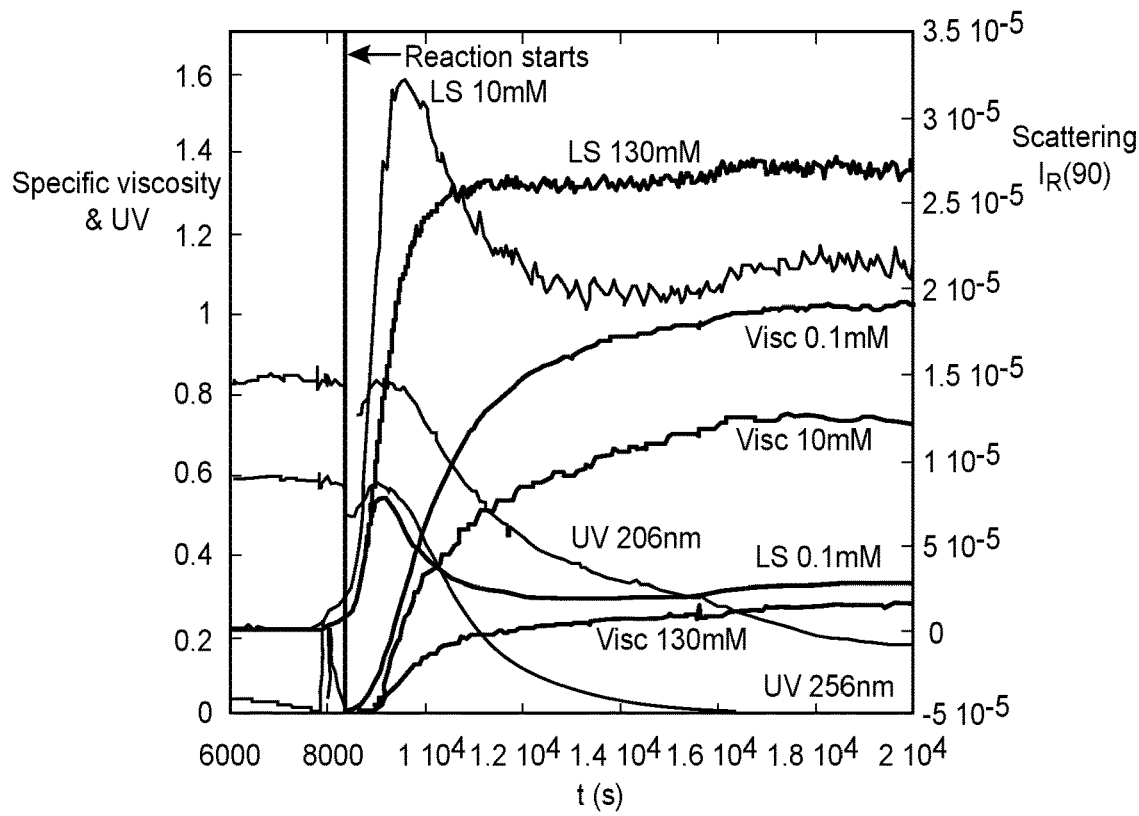
FIG. 4 shows the specific viscosity, UV, and light scattering data, with time, from a batch copolymerization of 50:50 acrylamide and styrene sulfonate using a serial flow device according to the present disclosure.

The reactions involved the free radical based synthesis of copolymeric polyelectrolytes, sometimes termed copolyelectrolytes. The electrically neutral monomer acrylamide ("Am") was copolymerized with the anionic monomer styrene sulfonate ("SS"). Because the reactivity ratios are widely separated, $r_{SS}$=2.14 and $r_{Am}$=0.18, there is strong composition drift during batch reactions. FIG. 4 shows representative raw data from a batch copolymerization in which the mole/mole ratio of Am/SS was 50/50.

The conformations, dimensions, hydrodynamics, and interactions of polyelectrolytes are very sensitive to the linear charge density $\xi$ of the polyelectrolyte and the IS of the supporting liquid medium. It is well known that decreasing IS at a fixed $\xi$ decreases ionic shielding along the polyelecrolyte chain causing it to swell from the increased intrapolymer electrostatic repulsion and to increase the interpolymer excluded volume, both due to the expansion of the polyelectrolyte, and to the interaction of the increased electrostatic potentials of the polyelectrolytes. See Reference 40. The swelling of the polyelectrolyte is manifested in terms of increased intrinsic viscosity [η], and the swelling and increased electrostatic interactions both increase the second, third, and higher virial coefficients, $A_2$, $A_3$, etc. The device of this example, having both a viscosity and light scattering detector at each IS stage is capable of measuring the intrinsic viscosity and virial coefficients. The increase in virial coefficients decreases light scattering intensity. In the limit of q=0 (scattering angle 0) the absolute Rayleigh scattering ration $I_R$ is given by $$I_R = \frac{Kc}{1/M_w + 2A_2c + 3A_cc^2} \quad (2)$$

where c is the polymer concentration, $M_w$ the weight average molar mass, and K is an optical constant, given for vertically polarized incident light by $$K = \frac{4\pi^2 n^2 (dn/dc)^2}{N_A \lambda^4} \quad (3)$$

where n is the solvent index of refraction, $\lambda$ is the vacuum wavelength of the incident light, $d\sigma/dc$ is the differential refractive index for the polymer in the chosen solvent, and q is the usual scattering wave-vector $q=(4\pi n/\lambda)\sin(\theta/2)$, where $\theta$ is the scattering angle. While the seven flow through detectors are at $\theta=90°$ and hence not at $q=0$, the trends at $90°$ for polymers of this size ($<10^6$ g/mole) will qualitatively follow those at $0°$. In the device it is possible to add more angles to each light scattering detector so as to make angular extrapolations to $q=0$.

At 0.1 mM the LS quickly rises to a maximum as the synthesis progresses (the vertical bar in the figure indicates when the polyelectrolyte synthesis reaction begins), as shown in FIG. 4. The increase in LS is due to formation of the polymer chains which scatter light. The fact that a maximum is reached is due to the action of both $A_2$ and $A_3$ in equation 2. The $A_3$ term in equation 2 then leads to the decrease in LS after the peak. The slight rise in LS towards the end is due to the fact that the SS consumes itself very quickly, due to its high reactivity ratio, so that towards the end of the reaction pure acrylamide homopolymer is produced, which has a higher molar mass than the copolyelectrolyte, The total solution viscosity $\eta(t)$ is measured by the pressure drop across the single capillary viscometer according to Poisseuille's law (see Reference 29), and $\eta(t)$ is related to the solvent viscosity $\eta_{solvent}$, the polymer intrinsic viscosity $[\eta]$, and the polymer concentration c by $$\eta(t)=\eta_{solvent}([\eta]c+\kappa_H[\eta]^2c^2+\ldots) \quad (4)$$

where $\kappa_H$ is a dimensionless hydrodynamic interaction constant, typically equal to 0.4 for neutral coil polymers, and less for charged ones. The specific viscosity $\eta_{sp}(t)$ is defined as $$\eta_{sp}(t) = \frac{\eta(t)-\eta_{solvent}}{\eta_{solvent}} \quad (5)$$

$[\eta]$ for a polymer is given by $$[\eta] = \frac{V_H}{M} \quad (6)$$

where $V_H$ is the hydrodynamic volume of the polymer and M its molar mass.

At 0.1 mM it is seen in FIG. 4 that $\eta_{sp}(t)$ increases monotonically to its final value, which is higher than all the other IS, since $V_H$ is at its largest from the swollen polyelectrolytes at low IS.

Considering now the LS at 10 mM IS the increased IS has shrunken the coil size and hence decreased $[\eta]$, $A_2$, and $A_3$, seen in FIG. 4. As a consequence, while LS still reaches a peak, this peak is higher than for 0.1 mM IS because $A_2$ and $A_3$ are smaller in the 10 mM case than in the 0.1 mM case. In contrast $\eta_{sp}(t)$ decreases since $V_H$, and hence $[\eta]$ decreases (equation 5) with the polymer chain shrinkage. $\eta_{sp}(t)$ continues to decrease for both the 50 mM and 100 mM IS cases.

At 130 mM IS the light scattering no longer has a peak, indicating that $A_3$ is now so small as to be negligible but that $A_2$ still has an effect. The scattering level ends higher than LS at the other IS, since $A_2$ and $A_3$ have their lowest values at the highest IS.

Also shown in FIG. 4 are the values of UV absorption at 206 nm and 255 nm. These can be used to compute the concentrations of each monomer as a function of time $c_{SS}(t)$ and $c_{Am}(t)$. The total fractional monomer mass conversion is defined as the total amount of concentration of polymer divided by the total initial mass of monomer $$f(t) = \frac{c_{Am}(0)+c_{SS}(0)-c_{Am}(t)+c_{SS}(t)}{c_{Am}(0)+c_{SS}(0)} \quad (7)$$

With knowledge of $c_{SS}(t)$ and $c_{Am}(t)$ the instantaneous fractional mass composition of polymer chains being formed at any instant t is $$F_{inst,Am}(t) = \frac{dc_{Am}(t)}{d(c_{Am}(t)+c_{SS}(t))} \quad (8a)$$

$$F_{inst,SS}(t) = \frac{dc_{SS}(t)}{d(c_{Am}(t)+c_{SS}(t))} \quad (8b)$$

where $F_{inst,Am}(t)$ is the instantaneous fraction by mass of Am in a copolymer chain at t, and likewise for $F_{inst,SS}$. These latter quantities hence follow the composition drift of the copolymers during the synthesis. Such a way of treating copolymer composition and drift by ACOMP has been described in, for example, Reference 41.

Figure 5:
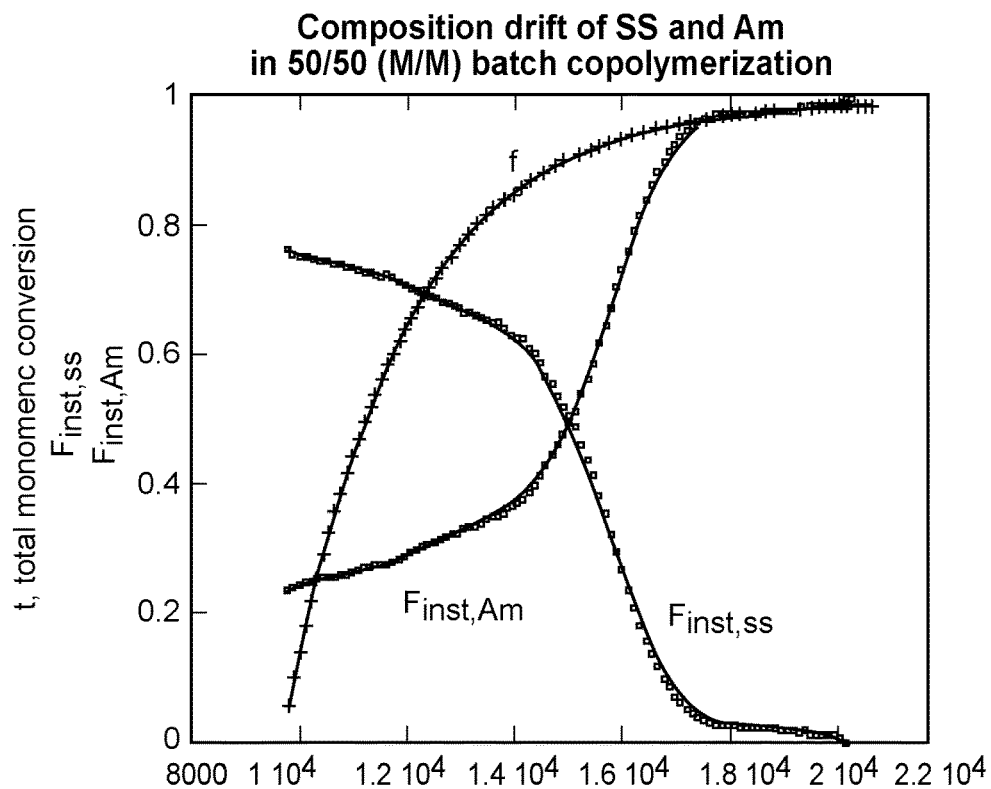
FIG. 5 shows the composition drift of monomers over time in a batch copolymerization of 50:50 acrylamide and styrene sulfonate using a serial flow device according to the present disclosure.

The UV signals lead to f, $F_{inst,Am}$ and $F_{inst,SS}$ found in FIG. 5.

A semi-batch reaction was also performed in which the starting reactor solution contained only Am in water and a reservoir solution containing SS was flowed in at a constant rate. This led to the opposite case of the batch reaction; starting with Am means neutral polymer chains are initially produced and, as the SS flows into the reactor, chains are produced with increasing SS composition, and hence increasing 4.

Figure 6:
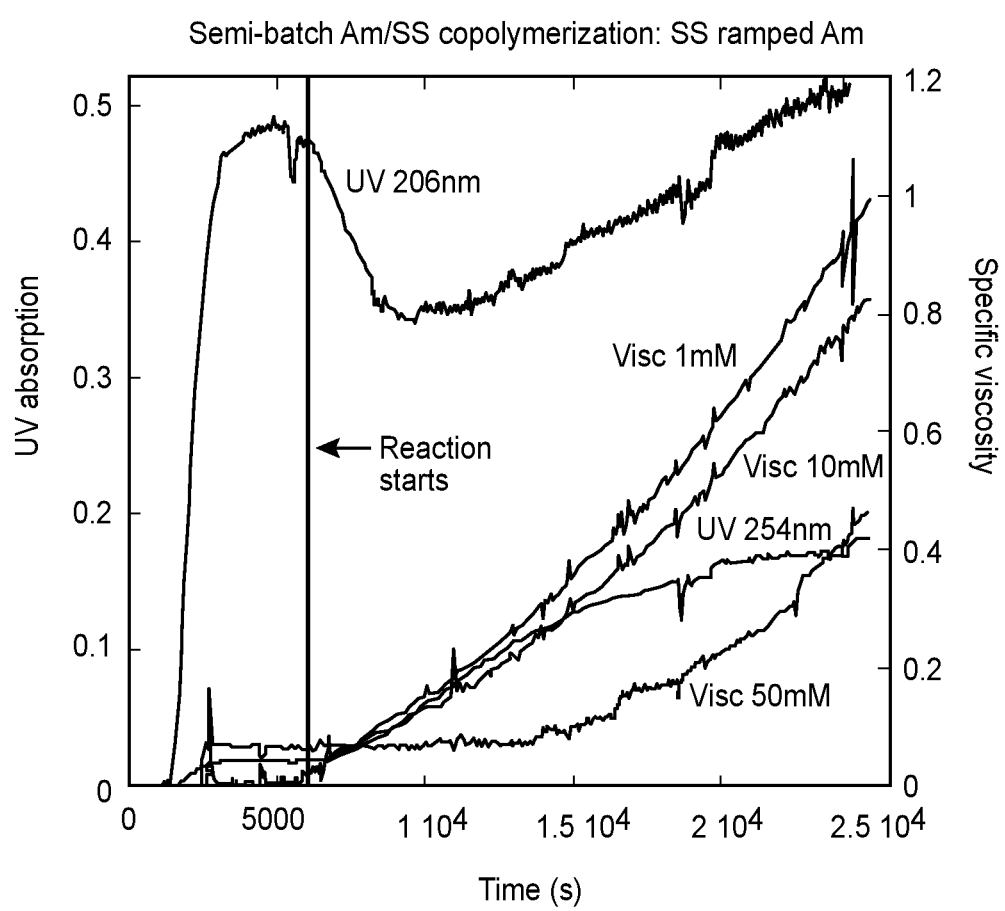
FIG. 6 shows the specific viscosity, UV, and light scattering data, with time, from a semi-batch copolymerization reaction wherein styrene sulfonate monomer was added to acrylamide using a serial flow device according to the present disclosure.

FIG. 6 shows the UV absorption at 206 nm and 254 nm, which is independent of IS and which was measured at only a single IS. Also shown in FIG. 6 is the specific viscosity with time, which falls markedly at any given time for increasing IS from 1 mM to 10 mM to 50 mM.

Figure 7A:
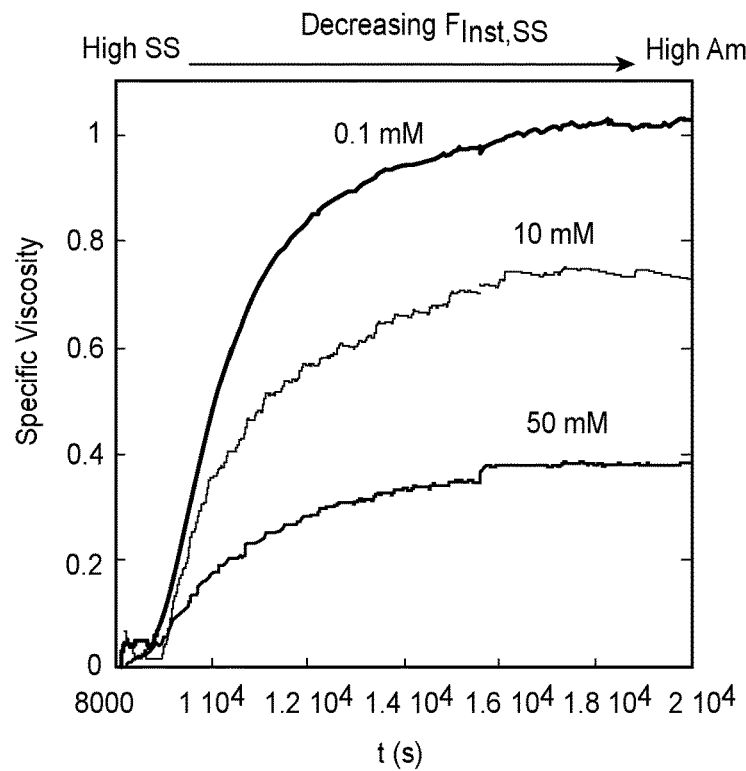
FIG. 7(A-B) shows the contrast in behavior for $\eta_{sp}(t)$ in the batch reaction (FIG. 7A) and the semi-batch reaction (FIG. 7B) between acrylamide and styrene sulfonate using a serial flow device according to the present disclosure.
Figure 7B:
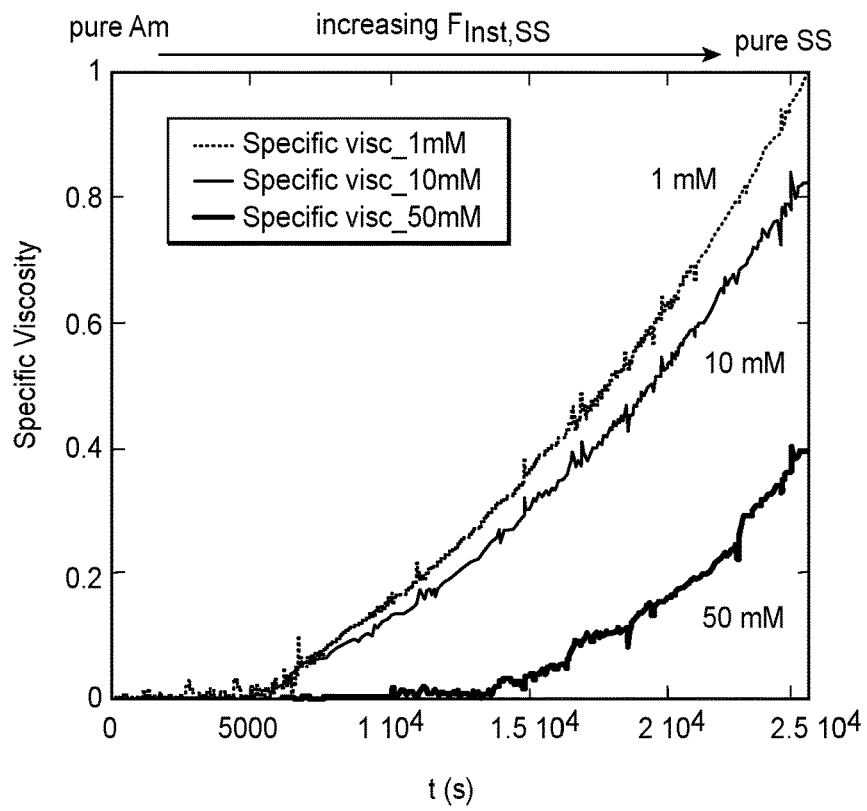

FIGS. 7a and 7b contrast the behavior for $\eta_{sp}(t)$ in the batch reaction and the semi-batch reaction, respectively. In FIG. 7a, SS is used up quickly in the batch reactor, leading to ever increasing concentration of neutral Am in the polymers in the reactor. Since Am is electrically neutral specific viscosity increases less and less with time, as the SS is used up and Am becomes dominant, seen by the concave downwards curvature, that is, by a negative second derivative of specific viscosity vs time. In FIG. 7b increasing the amount of electrically charged SS, by the semi-batch flow of SS containing solution into the reactor, leads to increased swelling of the polyelectrolyte chains, leading to concave upwards curvature, that is a positive second derivative of specific viscosity vs time. In both the batch and semi-batch cases, the specific viscosity at any instant is lower in the order of increasing ionic strength.

REFERENCES

This application incorporates herein by reference U.S. patent application Ser. No. 12/479,052 (Methods and Instrumentation for During-synthesis monitoring of polymer functional evolution); and U.S. Pat. No. 6,653,150 (Automatic Mixing and Dilution Methods for Online Characterization); and U.S. Pat. No. 8,322,199 (Two-Stage Polymer Analysis System and Method Using Automatic Dilution).

1. Hawker, C. J.; Bosman, A. W.; Harth, E., "New polymer synthesis by nitroxide mediated living radical polymerizations", Chem. Rev. 2001, 101, 3661-3688.
2. Mayadunne, R. T. A.; Rizzardo, E., "Mechanistic and Practical Aspects of RAFT Polymerization", in Living and Controlled Polymerization: Synthesis, Characterization and Properties of the Respective Polymers and Copolymers; Jagur-Grodzinski, J., Ed.; Nova Science Publishers: New York, 2005, 65.
3. Moad, G.; Rizzardo, E.; Thang, S. H., "Living radical polymerization by the RAFT process—A first update", Aust. J. Chem. 2006, 59, 669-692.
4. Barner, L.; Davis, T. P.; Stenzel, M.; Barner-Kowollik, C., "Complex macromolecular architectures by reversible addition fragmentation chain transfer chemistry: theory and practice", Macromol. Rapid Commun. 2007, 28, 539-559.
5. Matyjaszewski, K.; Ziegler, M. J.; Arehart, S. V.; Greszta D.; Pakula T., "Gradient copolymers by atom transfer radical copolymerization", J. Phys. Org. Chem. 2000, 13, 775-786.
6. Matyjaszewski, K., "Comparison and classification of controlled/living radical polymerizations". Matyjaszewski, K., Ed., Controlled/living radical polymerization. Progress in ATRP, NMP, and RAFT ACS symposium series vol. 768, ACS, Washington, DC 2000, 2-26.
7. Teoh, R. L.; Guice, K. B.; Loo, Y.-L., "Atom Transfer Radical Copolymerization of Hydroxyethyl Methacrylate and Dimethylaminoethyl Methacrylate in Polar Solvents", Macromolecules 2006, 39, 8609-8615.
8. Braunecker W. A.; Matyjaszewski, K., "Controlled/Living Radical Polymerization: Features, Developments, and Perspectives", Progr. Polym. Sci. 2007, 32, 93-146.
9. Maynard, H. D.; Heredia, K. L.; Li, R. C.; Parra, D. P.; Vazquez-Dorbatt, V., "Thermoresponsive biohybrid materials synthesized by ATRP", J. Mat. Chem. 2007, 17, 4015-4017.
10. Heredia, K. L.; Tolstyka, Z. P.; Maynard, H. D., "Aminooxy End Aminooxy End-Functionalized Polymers Synthesized by ATRP for Chemoselective Conjugation to Proteins", Macromolecules 2007, 40, 4772-4779.
11. Russell, A. J.; Lele, B. S.; Murata, H. Matyjaszewski, K., "Synthesis of uniform polymer-protein conjugates by initiating controlled radical polymerization from protein", Biomacromolecules 2005, 6, 3380-3387.
12. Purcell, I. P.; Lu, J. R.; Thomas, R. K.; Howe, A. M.; Penfold, J., "Adsorption of Sodium Dodecyl Sulfate at the Surface of Aqueous Solutions of Poly(vinylpyrrolidone) Studied by Neutron Reflection." Langmuir 1998, 14, 1637-1645.
13. Li, T.; Xu, R.; Bloor, D. M.; Penfold, J.; Holzwarth, J. F.; Wyn-Jones, E., "Moderation of the Interactions between Sodium Dodecyl Sulfate and Poly(vinylpyrrolidone) Using the Nonionic Surfactant Hexaethylene glycol Mono-n-dodecyl Ether C12E06: an Electromotive Force, Microcalorimetry, and Small-Angle Neutron Scattering Study." Langmuir 2000, 16, 8677-8684.
14. Interactions of Surfactants with Polymers and Protein; Goddard, E. D. Ananthapadamanabhan, K. P. Eds; CRC Press: Boca Raton, Fl., 1993.
15. Colloid-Polymer Interactions, Farinato, R. S.; Dubin, P. L. Eds., John Wiley and Sons, 1999.
16. Tang, Y.; Liu, S. Y.; Armes, S. P.; Billingham, N. C., "Solubilization and controlled release of a hydrophobic drug using novel micelle-forming ABC triblock copolymers", Biomacromolecules 2003, 4, 1636-1645.
17. Chen, W. X; Fan, X. D.; Huang, Y.; Liu, Y. Y; Sun, L., "Synthesis and characterization of a pentaerythritol-based amphiphilic star block copolymer and its application in controlled drug release", Reactive & Functional Polymers 2009, 69, 97-104.
18. Park, M.-K.; Deng, S.; Advincula, R., "Sustained Release Control via Photo-Cross-Linking of Polyelectrolyte Layer-by-Layer Hollow Capsules", Langmuir 2005, 21, 5272-5277.
19. Richter, A.; Wenzel, J.; Kretschmer, K., "Mechanically adjustable chemostats based on stimuli-responsive polymers", Sensors and Actuators, B: Chemical 2007, B125, 569-573.
20. Lochhead, R. Y., "The role of polymers in cosmetics: recent trends", ACS Symposium Series 2007, 961 (Cosmetic Nanotechnology: Polymers and Colloids in Cosmetics), 3-56.
21. Kulkarni, S.; Malmstadt, N.; Hoffman, A. S.; Stayton, P. S., "Micro and nanoscale smart polymer technologies in biomedicine", BioMEMS and Biomedical Nanotechnology 2006, 3, 289-304.
22. Jaycox, G. D., "Stimuli-responsive polymers. 9. Photoregulation of optical rotations in chiral polyesters: Altering responsive outputs with conformationally flexible backbone elements", Polymer 2007, 48, 82-90.
23. Winnik, F. M.; Whitten, D. G.; Urban, M. W.; Lopez, G., "Stimuli-Responsive Materials: Polymers, Colloids, and Multicomponent Systems", Langmuir 2007, 23, 1-2.
24. Schmaljohann, D., "Thermo- and pH-responsive polymers in drug delivery", Advanced Drug Delivery Rev. 2006, 58, 1655-1670.
25. Alarcon, C. de las Heras; Pennadam, S.; Alexander, C., "Stimuli responsive polymers for biomedical applications", Chem. Soc. Rev. 2005, 34, 276-285.
26. Raez, J.; Tomba, J. P.; Manners, I.; Winnik, M. A., "A reversible tube-to-rod transition in a block copolymer micelle", JACS 2003, 125, 9546-9547.
27. A. Paril, A. M. Alb, W. F. Reed, "Online Monitoring of the Evolution of Polyelectrolyte Characteristics during Postpolymerization Modification Processes", Macromolecules, 40, 4409-4413, 2007.
28. G. A. Sorci, W. F. Reed, "Electrostatic and Association Phenomena in Aggregates of Polymers and Micelles", Langmuir, 18, 353-364, 2002.
29. R. Strelitzki, W. F. Reed, "Automated Batch Characterization of Polymer Solutions by Static Light Scattering and Viscometry", J. App. Polym. Sci., 73, 2359-2368 1999.
30. McFaul, Colin A. et al., "Simultaneous Multiple Sample Light Scattering Detection Of LCST During Copolymer Synthesis", Polymer, 2011, 4825-4833.
31. Reed, Wayne F. et al., "Online, continuous monitoring of the sensitivity of the LCST of NIPAM-Am copolymers to discrete and broad composition distributions", Polymer, 2014, 4899-4907.
32. Reed, Wayne, Device & Method for monitoring the presence, onset and evolution of particulates in chemically or physically reacting systems, U.S. patent application Ser. No. 13/985,560, filed Nov. 26, 2013.
33. Reed, Wayne, Device & Method for monitoring the presence, onset and evolution of particulates in chemically or physically reacting systems, PCT/US2012/025041, filed Feb. 14, 2012.

34. Reed, Wayne et al., Characterization of Polymer and Colloid Solutions, PCT/US2014/464658, filed Aug. 20, 2014.
35. Reed, Wayne et al., Method and devices for simultaneously monitoring colloid and polymer characteristics during heterogeneous phase polymerization reactions, U.S. Pat. No. 7,716,969, filed Oct. 1, 2007.
36. Reed, Wayne, Miniature, Submersible, Versatile, Light Scattering Probe for Absolute Equilibrium and Non-equilibrium Characterization of Macromolecular and Colloidal Solutions, U.S. Pat. No. 6,052,184, filed Nov. 13, 1997.
37. Reed, Wayne, Device and Method of Simultaneously Measuring the Light Scattering from Multiple Liquid Samples Containing Polymers and/or Colloids, U.S. Pat. No. 6,618,144, filed Oct. 16, 2000.
38. Reed, Wayne, Automatic Mixing and Dilution Methods for Online Characterization of Equilibrium and Non-Equilibrium Properties of Solutions Containing Polymers and/or Colloids, U.S. Pat. No. 6,653,150, filed Sep. 23, 1999.
39. D. P. Norwood, W. F. Reed "Comparison of Single Capillary and Bridge Viscometers as Size Exclusion Chromatography Detectors", Int. J. Polym. Ana. and Char., 4, 99-132, 1997.
40. S. Foerster, M. Schmidt, M. "Polyelectrolytes in solution", Adv. Polym. Sci., 120, 53-95, 1995.
41. A. Giz, A. Oncul Koc, H. Giz, A. M. Alb, W. F. Reed "Online monitoring of reactivity ratios, composition, sequence length, and molecular weight distributions during free radical copolymerization", Macromolecules, 35, 6557-6571, 2002.
42. *Smart Materials: Technologies and Global Markets.* BCC Research, May 1, 2011.
43. Zhuang, J. M., M. R. Gordon, J. Ventura, L. Y. Li, and S. Thayumanavan, "Multi-stimuli responsive macromolecules and their assemblies." Chemical Society Reviews, 2013, 42, 7421-7435.
44. Jeong, B. and A. Gutowska, "Lessons from nature: stimuli-responsive polymers and their biomedical applications." Trends in Biotechnology, 2002, 20, 305-311.
45. Nath, N. and A. Chilkoti, "Creating "Smart" surfaces using stimuli responsive polymers." Advanced Materials, 2002, 14, 1243-1247.
46. Liu, F. and M. W. Urban, "Recent advances and challenges in designing stimuli-responsive polymers." Progress in Polymer Science, 2010, 35, 3-23.
47. Galaev, I. and B. Mattiasson, eds. *Smart Polymers: Applications in Biotechnology and Biomedicine.* second ed. 2007, CRC Press, Boca Raton
48. Chung, J. E., M. Yokoyama, M. Yamato, T. Aoyagi, Y. Sakurai, and T. Okano, "Thermo-responsive drug delivery from polymeric micelles constructed using block copolymers of poly(N-isopropylacrylamide) and poly(butylmethacrylate)." Journal of Controlled Release, 1999, 62, 115-127.
49. Zhang, J. and N. A. Peppas, "Synthesis and characterization of pH- and temperature-sensitive poly(methacrylic acid)/poly(N-isopropylacrylamide) interpenetrating polymeric networks." Macromolecules, 2000, 33, 102-107.
50. Jain, S. and F. S. Bates, "On the origins of morphological complexity in block copolymer surfactants." Science, 2003, 300, 460-464.
51. Alina M. Alb, Michael F. Drenski, Wayne F. Reed, "Simultaneous continuous, non-chromatographic monitoring and discrete chromatographic monitoring of polymerization reactions", J. Appl. Polym. Sci., 13, 190-198, 2009.

Additional Aspects (1) In one aspect, disclosed herein is a device for measuring the characteristics of a liquid and the contents thereof, comprising:
  a chemical reactor;
  a means for automatically extracting the liquid from the chemical reactor and providing a continuous reactor flow;
  means for making successive serial additions into the liquid; and
  one or more measuring instruments interposed between one or more liquid-addition stages through which the liquid flows in serial fashion.

(2) The device of aspect (1) wherein the contents of the liquid are one or more of the following; polymers, monomers, nanoparticles, colloids, micelles, aggregates, microgels, microcrystals, liposomes, vesicles, emulsions.

(3) The device of aspect (1) wherein the serial additions into the liquid change one or more of the following characteristics of the liquid: pH, ionic strength (4) The device of aspect (1) wherein the liquid contains one or more of the following; polymers, monomers, nanoparticles, colloids, micelles, aggregates, microgels, microcrystals, liposomes, vesicles, and emulsions.

(5) The device of aspect (1) wherein the liquid contains stimuli-responsive polymers.

(6) The device of aspect (1) wherein the chemical reactor is used to for polymerization reactions.

(7) The device of aspect (1) wherein the chemical reactor and means for automatically extracting liquid from the chemical reactor and providing a continuous reactor liquid flow are provided by an ACOMP system (U.S. Pat. No. 6,653,150.)

(8) The device of aspect (1) wherein the liquid is conditioned and diluted.

(9) The device of aspect (1) wherein the liquid is conditioned and diluted using the device and methods of U.S. Pat. No. 6,653,150.

(10) The device of aspect (1) wherein the means for making successive serial additions changes the conditions of the liquid.

(11) The device of aspect (10) wherein the conditions of the liquid changed include one or more of the following: pH, ionic strength, added small molecules, polarity, solvent composition, added surfactants, polymers, and specific ions.

(12) The device of aspect (1) wherein the one or more measuring instruments are selected from the following: pH, conductivity, single or multi-angle total intensity light scattering, dynamic light scattering, Mie scattering, fluorescence, turbidity, viscosity, refractometer, polarimeter, circular dischroism, near or mid-infrared, and Raman detection.

(13) The device of aspect (1) wherein one or more measuring instruments yield characteristics of polymers and/or colloids in the flowing stream.

(14) The device of aspect (1) wherein the means for making successive serial additions represents cumulative formulation steps.

(15) The device of aspect (14) wherein the effects of the formulation steps on polymers and/or colloids in the liquid is measured by the one or more measuring instruments interposed between one or more liquid-addition stages through which the liquid flows in serial fashion.

(16) The device of aspect (1) wherein an LMPC is used for a first dilution, mixing the flowing, extracted liquid with a first solvent to achieve a desired level of dilution and produce a flowing solution of said diluted liquid.

(17) A device for measuring the characteristics of a liquid and the contents thereof, comprising:
a chemical reactor;
means for automatically extracting liquid from the chemical reactor and providing a continuous flow;
means for making successive serial additions into the flowing, extracted liquid;
one or more measuring instruments interposed between one or more liquid-addition stages through which the liquid flows in serial fashion; and
one or more means for evaluating the measurements of the one or more measuring instruments in order to automatically adjust and control the means for making the successive serial additions into the flowing, extracted liquid.

(18) The device of aspect (17) wherein the automatic adjustments to serial additions are made by controlling pump rates.

(19) The device of aspect (17) wherein the means for making the successive serial additions is selected from the following: temperature, pH, ionic strength, presence of specific ions, small molecules, polarity, and surfactants.

(20) A method of measuring the characteristics of a liquid and the contents thereof, comprising the steps of:
automatically extracting a continuous stream of liquid from a chemical reactor;
making a first dilution of said stream to produce a continuously flowing stream of diluted reactor contents;
adding liquid at one or more dilution stages to change the nature of the flowing stream of diluted reactor contents; and
measuring the properties of the flowing stream of diluted reactor contents and the liquid stream contents with instruments interposed between the one or more dilution stages.

(21) The method of aspect (20) wherein the steps of automatically extracting a continuous stream of liquid from a chemical reactor and making a first dilution of said stream to produce a continuously flowing stream of diluted reactor contents is accomplished by using an ACOMP device (U.S. Pat. No. 6,653,150.)

The foregoing description is given for clearness of understanding only, and no unnecessary limitations should be understood therefrom, as modifications within the scope of the invention may be apparent to those having ordinary skill in the art.

The terms "comprising" and "including" and "having" and "involving" (and similarly "comprises", "includes," "has," and "involves") and the like are used interchangeably and have the same meaning. Specifically, each of the terms is defined consistently with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

Wherever any of the phrases "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

I claim:

1. A device 100 comprising:
   (a) a sample reservoir 101 containing a sample comprising a polymer or a colloid, the sample reservoir 101 comprising a sample reservoir outlet conduit 101*c*;
   (b) a first system 110 comprising:
      (i) a first mixing chamber 111 adapted to contain a first mixing chamber solution, the first mixing chamber comprising a sample inlet 111*a*, a first solvent inlet 111*b*, and a first mixing chamber outlet conduit 111*c*;
      (ii) a first sample pump 112 in fluid communication with the sample reservoir 101 and the first mixing chamber 111, the first sample pump 112 adapted to deliver the sample from the sample reservoir 101 through the sample reservoir outlet conduit 101*c* into the sample inlet 111*a* of the first mixing chamber 111;
      (iii) a first solvent reservoir 113 containing a first solvent, the first solvent reservoir 113 comprising a first solvent reservoir outlet conduit 113*c*, wherein the first solvent changes a first condition of the sample in the first mixing chamber solution, the first condition being selected from the group consisting of ionic strength, pH value, surfactant content, and solvent polarity;
      (iv) a first solvent pump 114 in fluid communication with the first solvent reservoir 113 and the first mixing chamber 111, the first solvent pump 114 adapted to deliver the first solvent from the first solvent reservoir 113 though the first solvent reservoir outlet conduit 113c into the first solvent inlet 111b of the first mixing chamber 111; and (v) a first detector train 115 comprising a first detector train inlet, a first detector train outlet, a first detector 115a between the first detector train inlet and the first detector train outlet, and a first additional detector 115b between the first detector train inlet and the first detector train outlet, wherein the first detector train 115 is in fluid communication with the first mixing chamber 111 through the first mixing chamber outlet conduit 111c of the first mixing chamber 111 and the first detector train inlet of the first detector train 115, the first detector 115a is configured to detect a property of the first mixing chamber solution, and the first additional detector 115b is configured to detect a property of the first mixing chamber solution;

(c) a second system 120 serial to, and downstream of, the first system 110, the second system 120 comprising:

(i) a second mixing chamber 121 connected to the first detector train 115 outlet and adapted to contain a second mixing chamber solution, the second mixing chamber 121 comprising a second mixing chamber inlet 121a, a second solvent inlet 121b, and a second mixing chamber outlet conduit 121c, the second mixing chamber 121 in fluid communication with the first detector train outlet;

(ii) a second solvent reservoir 123 containing a second solvent that is different from the first solvent, the second solvent reservoir 123 comprising a second solvent reservoir outlet conduit 123c, wherein the second solvent changes a second condition of the first mixing chamber solution in the second mixing chamber solution, the second condition being different from the first condition and being selected from the group consisting of ionic strength, pH value, surfactant content, and solvent polarity;

(iii) a second solvent pump 124 in fluid communication with the second solvent reservoir 123 and the second mixing chamber 121, the second solvent pump 124 adapted to deliver the second solvent from the second solvent reservoir 123 through the second solvent reservoir outlet conduit 123c into the second solvent inlet 121b of the second mixing chamber 121; and (iv) a second detector train 125 comprising a second detector train inlet, a second detector train outlet, a second detector 125a between the second detector train inlet and the second detector train outlet, and a second additional detector 125b between the second detector train inlet and the second detector train outlet, wherein the second detector train 125 is in fluid communication with the second mixing chamber 121 through the second mixing chamber outlet conduit 121c of the second mixing chamber 121 and the second detector train inlet of the second detector train 125, the second detector 125a is configured to detect a property of the second mixing chamber solution, and the second additional detector 125b is configured to detect a property of the second mixing chamber solution; and (d) a sample detector 105 configured to detect a property of the sample, the sample detector 105 being in fluid communication with the sample reservoir 101 and the first mixing chamber 111.

2. The device of claim 1, further comprising a third system 130 serial to, and downstream of, the second system 120, the third system 130 comprising:

(i) a third mixing chamber 131 connected to the second detector train 125 outlet and adapted to contain a third mixing chamber solution, the third mixing chamber 131 comprising a third mixing chamber inlet 131a, a third solvent inlet 131b, and a third mixing chamber outlet conduit 131c, the third mixing chamber in fluid communication with the second detector train outlet;

(ii) a third solvent reservoir 133 containing a third solvent that is different from the first solvent and second solvent, the third solvent reservoir 133 comprising a third solvent reservoir outlet conduit 133c, wherein the third solvent changes a third condition of the second mixing chamber solution in the third mixing chamber solution, the third condition being different from the first and second conditions and being selected from the group consisting of ionic strength, pH value, surfactant content, and solvent polarity;

(iii) a third solvent pump 134 in fluid communication with the third solvent reservoir 133 and the third mixing chamber 131, the third solvent pump 134 adapted to deliver the third solvent from the third solvent reservoir 133 through the third solvent reservoir outlet conduit 133c into the third solvent inlet 131b of the third mixing chamber 131; and (iv) a third detector train 135 comprising a third detector train inlet, a third detector train outlet, a third detector 135a between the third detector train inlet and the third detector train outlet, and a third additional detector 135b between the third detector train inlet and the third detector train outlet, wherein the third detector train 135 is in fluid communication with the third mixing chamber 131 through the third mixing chamber outlet conduit 131c of the third mixing chamber 131 and the third detector train inlet of the third detector train 135, the third detector 135a is configured to detect a property of the third mixing chamber solution, and the third additional detector 135b is configured to detect a property of the third mixing chamber solution.

3. The device of claim 2, further comprising a fourth system 140 serial to, and downstream of, the third system 130, the fourth system 140 comprising:

(i) a fourth mixing chamber 141 connected to the third detector train 135 outlet and adapted to contain a fourth mixing chamber solution, the fourth mixing chamber 141 comprising a fourth mixing chamber inlet 141a, a fourth solvent inlet 141b, and a fourth mixing chamber outlet conduit 141c, the fourth mixing chamber in fluid communication with the third detector train outlet;

(ii) a fourth solvent reservoir 143 containing a fourth solvent that is different from the first solvent, second solvent, and third solvent, the fourth solvent reservoir 143 comprising a fourth solvent reservoir outlet conduit 143c, wherein the fourth solvent changes a fourth condition of the third mixing chamber solution in the fourth mixing chamber solution, the fourth condition being different from the first, second, and third conditions and being selected from the group consisting of ionic strength, pH value, surfactant content, and solvent polarity;

(iii) a fourth solvent pump 144 in fluid communication with the fourth solvent reservoir 143 and the fourth mixing chamber 141, the fourth solvent pump 144 adapted to deliver the fourth solvent from the fourth solvent reservoir 143 through the fourth solvent reservoir outlet conduit 143c into the fourth solvent inlet 141b of the fourth mixing chamber 141; and (iv) a fourth detector train 145 comprising a fourth detector train inlet, a fourth detector train outlet, a fourth detector 145*a* between the fourth detector train inlet and the fourth detector train outlet, and a fourth additional detector 145*b* between the fourth detector train inlet and the fourth detector train outlet, wherein the fourth detector train 145 is in fluid communication with the fourth mixing chamber 141 through the fourth mixing chamber outlet conduit 141*c* of the fourth mixing chamber 141 and the fourth detector train inlet of the fourth detector train 145, the fourth detector 145*a* is configured to detect a property of the fourth mixing chamber solution, and the fourth additional detector 145*b* is configured to detect a property of the fourth mixing chamber solution.

4. The device of claim 1, wherein each of the first detector, the second detector, the sample detector, the first additional detector, and the second additional detector is a type selected from the group consisting of light scattering, ultraviolet/visible absorption, infrared absorption, refractometry, viscosity, conductivity, pH, polarimetry, turbidity, fluorescence, circular dichroism, Raman scattering, and birefringence.

5. The device of claim 1, wherein:
the first detector 115*a* and the first additional detector 115*b* detect light scattering and viscosity, respectively, and
the second detector 125*a* and the second additional detector 125*b* detect scattering and viscosity, respectively.

6. The device of claim 1, wherein:
the first detector 115*a* and the first additional detector 115*b* detect the same property under different conditions, and
the second detector 125*a* and the second additional detector 125*b* detect the same property under different conditions.

7. The device of claim 1, further comprising at least one of:
(i) a first system mixing chamber pump 116 in fluid communication with the first mixing chamber 111 and the first detector 115*a*, the first system mixing chamber pump 116 adapted to deliver the first mixing chamber solution from the first mixing chamber outlet conduit 111*c* of the first mixing chamber 111 to the first detector 115*a*; and (ii) a second system mixing chamber pump 126 in fluid communication with the second mixing chamber 121 and the second detector 125*a*, the second system mixing chamber pump 126 adapted to deliver the second mixing chamber solution from the second mixing chamber outlet conduit 121*c* of the second mixing chamber 121 to the second detector 125*a*.

8. The device of claim 2, further comprising a third system mixing chamber pump 136 in fluid communication with the third mixing chamber 131 and the third detector 135*a*, the third system mixing chamber pump 136 adapted to deliver the third mixing chamber solution from the third mixing chamber outlet conduit 131*c* of the third mixing chamber 131 to the third detector 135*a*.

9. The device of claim 1, wherein the sample reservoir 101 is a chemical reactor comprising a recirculation loop 160, and the first sample pump 105 is adapted to withdraw a small portion from the recirculation loop 160 as the sample delivered into the first mixing chamber 111.

10. The device of claim 1, wherein the sample reservoir 101 is an injection loop.

11. The device of claim 1, wherein the sample comprises the colloid.

12. The device of claim 1, wherein the sample comprises the polymer.

13. The device of claim 1, wherein:
the polymer or colloid comprises a stimuli-responsive polymer or colloid;
the stimuli-responsive polymer or colloid exhibits one or more stimuli-responses when the first solvent changes the first condition of the sample, when the second solvent changes the second condition of the first mixing chamber solution, or both; and
the stimuli-responses are selected from the group consisting of chain expansion, conformational change, coalescence, phase change, and micellization.

14. The device of claim 1, wherein:
the sample reservoir is a chemical reactor;
the device comprises a controller configured to change one or more reaction conditions in the chemical reactor based on a detected property in the first mixing chamber solution, a detected property in the second mixing chamber solution, or both.

\* \* \* \* \*